United States Patent [19]

Siler-Khodr

[11] Patent Number: 6,048,534
[45] Date of Patent: *Apr. 11, 2000

[54] METHODS AND COMPOSITIONS FOR THE SELECTIVE REGULATION OF CHORIONIC PROSTANOIDS

[75] Inventor: Theresa Siler-Khodr, San Antonio, Tex.

[73] Assignee: Board of Regents The University of Texas System, Austin, Tex.

[*] Notice: This patent is subject to a terminal disclaimer.

[21] Appl. No.: 08/476,125

[22] Filed: Jun. 7, 1995

Related U.S. Application Data

[63] Continuation-in-part of application No. 08/091,899, Jul. 15, 1993.
[51] Int. Cl.⁷ .......................... A61K 39/00; A61K 38/00; A01N 37/18
[52] U.S. Cl. ............................. 424/198.1; 514/2; 514/12
[58] Field of Search ..................... 514/2, 12; 424/198.1

[56] References Cited

U.S. PATENT DOCUMENTS 5,420,111  5/1995  Gluckman et al. .

FOREIGN PATENT DOCUMENTS

96/09065  3/1996  WIPO .

OTHER PUBLICATIONS

Vane et al., *British Journal of Pharmacology*, 48:629–39, 1973.
Johnson et al., *American Journal of Obstetrics and Gynecology*, 123(4):364–75, 1975.
Geisthovel. et al., *Human Reproduction*, 5(7):785–799, 1990.
Siler–Khodr, *38th Annual Meeting of the Society for the Study of Reproduction*, (Raleigh, NC), Abstract#513:178, 1992.

*Primary Examiner*—Anthony C. Caputa
*Assistant Examiner*—Mark Navarro
*Attorney, Agent, or Firm*—Locke Liddell & Sapp LLP; Denise L. MayField

[57] ABSTRACT

Methods for inhibiting the production of specific vasoconstrictive prostanoids, such as thromboxane and prostaglandin $F_{2\alpha}$, through the addition of insulin-like growth factor, particularly IGF-I or IGF-II, to human placental cells are disclosed. IGF-I is demonstrated to avoid affecting material and placental production of prostaglandin $E_2$, human chorionic gonadotropin, PGFM, and 6-keto-PGF1-alpha by placental cells. Improved methods for vasoregulation of vasoconstrictive diseases of pregnancy are also disclosed. Methods for treating intrauterine growth retardation and hypertension with IGF-I are described. Improved methods for inhibiting pre-term labor are provided. Methods for inducing labor with agents that specifically inhibit insulin-like growth factor are also disclosed. Such inhibitors of IGF-I include antibodies, antagonists of IGF-I, and metabolizing enzymes of IGF-I.

8 Claims, 21 Drawing Sheets

METHODS AND COMPOSITIONS FOR THE SELECTIVE REGULATION OF CHORIONIC PROSTANOIDS

The present application is a continuation-in-part of co-pending U.S. patent application Ser. No. 08/091899 filed Jul. 15, 1993, the entire text and figures of which disclosure is specifically incorporated herein by reference without disclaimer.

The United States government has rights in the present application as research to the developement of the invention was partially supported by NIH grant 21708 and HD 10202.

FIELD OF THE INVENTION

The present invention relates generally to the field of prostanoid regulation. In particular, the invention relates to a method for regulating specific placental prostanoids. In one example the invention relates to regulation of placental prostanoids to relieve symptoms of intrauterine growth retardation and hypertension.

BACKGROUND OF THE INVENTION

Nearly 11% (approximately 225,000 a year) of all pregnancies in the United States result in pre-term delivery. Such a record results in a significant incidence of perinatal morbidity and mortality. Despite major advances in neonatal care, retention of the fetus in utero is preferred in most instances. However, the desire to prolong intrauterine development must be balanced against the risks of continued pregnancy to both the mother and fetus, as well as the risks of concurrently available forms of pharmacological intervention. In general, the use of tocolytic agents to prolong pregnancy is reserved for those cases where the gestational age is greater than 20 weeks and less than 34 to 36 weeks.

There are several indications for, and contraindications to, the clinical use of agents that inhibit labor by inhibiting uterine contractions. The clearest indications for such agents are (1) to delay or prevent premature parturition in selected individuals and (2) to slow or arrest delivery for brief periods in order to undertake other therapeutic measures. Tocolytic agents that are currently in use for inhibiting contractions include $\beta_2$-adrenergic agonists, magnesium sulfate, ethanol, and inhibitors of prostaglandin synthesis, such as indomethacin. The use of tocolytic agents has been reviewed in several symposia (Symposium, 1981, 1982) and by Caritis (1983).

In the current practice of obstetrics, the use of indomethacin, which is an enzyme inhibitor, to inhibit prostaglandins in the treatment of premature labor prior to 33 weeks of gestation, is an accepted medical practice. However, enzyme inhibitors of prostaglandin synthesis, such as indomethacin, can unnecessarily prolong gestation in term pregnancies. In addition, the use of indomethacin in premature labor has been curtailed because of concern for its potential for causing adverse effects in the fetus. Of particular importance is the possibility of premature closure of the ductus arteriosus and the production of pulmonary hypertension from use of indomethacin. In addition, relatively high molar concentrations of indomethacin are necessary to produce pharmacological affects, on the order to at least $10^{-3}$ molar (M).

For example, the indiscriminate inhibition of several vasodilatory and vasoconstrictive prostanoids by indomethacin (prostaglandin $E_2$, prostaglandin $F_{2\alpha}$, prostacyclin, thromboxane $A_2$) is believed to be related to the incidence of serious complications to mother and fetus from the use of this agent in vivo. For example, inhibition of prostacyclin in the pregnant animal can result in vasoconstriction; while inhibiting $PGE_2$ can result in premature closure of the fetal ductus arteriosus. While fetal echocardiography can detect early signs of constriction of the ductus arteriosus, and its use may permit the continued administration of indomethacin or related agents in those instances where evidence of ductal construction is absent (Moise et al., 1988), the risk of these serious side effects make the treatment undesirable. The potentially serious side affects observed with currently employed regimens for managing labor, particularly with the use of indomethacin through the control of prostaglandin synthesis, continues to prompt research efforts to identify the mechanisms involved in the onset and progression of labor.

Prostanoids are a family of autacoids (formed from arachidonic acid) thought to play an important role during implantation, in the progress and maintenance of pregnancy, and during the initiation and progress of labor (Angle and Johnston, 1990). Placental prostanoid production is considered to be important during labor as well as throughout pregnancy, in regulating vascular tone, as well as affecting other hormonal production (Myatt, 1990). In human pregnancy, multiple sites of chorionic prostanoid production have been identified, i.e., the amnion, the chorion, the decidua and the placenta (Duchesne et al., 1978; Mitchell et al., 1978a, 1978b, 1978c; Robinson et al., 1979; Haning et al., 1982; Olson et al., 1983; Harper et al., 1983; Siler-Khodr et al., 1986b). In addition to its role in prostanoid production, the placenta also has multiple paracrine and endocrine capacities in human pregnancy. Although it is recognized that prostanoids such as prostaglandin $E_2$, prostaglandin $F_{2\alpha}$, the metabolite of $PGF_{2\alpha}$, 13,14-dihydro-, 15-keto-prostaglandin $F_{2\alpha}$ (PGFM), thromboxane $A_2$ ($TxB_2$) and prostacyclin ($PGI_2$) are all produced by placental tissue, the quantities of these substances, relative to the size of the placenta is frequently not appreciated. In addition, while the placenta is known to be an important site of prostanoid production, little is known of factors controlling the production of these prostanoids from human placental tissues.

Abnormal placental prostanoid production has been reported in diseases of pregnancy, including pregnancy-induced hypertension and intra-uterine growth retardation (Demers and Gabbe, 1976; Robinson et al., 1979; Hillier and Smith, 1981; Valenzuela and Bodhke, 1980; Jogee et al., 1983; Walsh, 1985). One of the multiple causes of intrauterine growth retardation (IUGR) is defective uteroplacental perfusion (Arias and Tomich, 1982). The placenta in pregnancies complicated by IUGR may show a maternal defect in the vascular response to placentation, even without hypertensive disease (Khong et al., 1986). Although the control of placental blood flow in normal pregnancy is not well understood, placental prostanoids are thought to play a role in local vaso-regulation (Magness and Rosenfeld, 1992). However, very few studies have been done on the control of human placental prostanoid release.

Insulin-like growth factor (IGF-I), also commonly known as somatomedin-C, is a growth factor that is well known for its stimulation of cellular proliferation, and is recognized as the principal mediator of the action of growth hormone. (Murphy et al., 1990). The IGFs are known to circulate in relatively high concentrations in the body, despite the fact that they are synthesized in many, if not most, tissues. The known activity of IGF-I in mediating growth hormone is consistent with the observation made by others that it may enhance fetal growth. IGF-I has not been described as important in vasoregulation, pregnant or non-pregnant, or in regulating placental vasoregulation or vasoconstriction, and therefore, the use of IGF-I for hypertension has not been examined. In addition, in cases of IUGR, the use of IGF-I for vasoregulation of the placenta has not been examined. Neither has IGF-I been described as important in the onset or during the progression of labor, and therefore, the use of IGF-I during labor has also not been examined. Nor has IGF-I been described as related to the activity of prostaglandins or prostanoids.

SUMMARY OF THE INVENTION

The present invention provides methods for improving vaso-regulation in abnormal pregnancies such as pregnancy-induced hypertension and intrauterine growth retardation (IUGR), without the potential for risk to the fetus or mother associated with use of other common pharmaceutically used drugs that modulate prostaglandin production, such as indomethacin.

Insulin-like growth factor I (IGF-I) is a hormone that is demonstrated by the present inventor to be particularly useful at relatively low molar concentrations, on the order of $10^{-9}$ molar in producing a selective pharmacological affect on human placental tissue.

More specifically, IGF-I is demonstrated to provide a specific and effective inhibition of the production of particular vaso-constrictive chorionic prostanoids, particularly thromboxane and prostaglandin $F_{2\alpha}$ by human placental cells, without inhibiting the production of vaso-dilating prostanoids, such as prostacyclin ($PGI_2$) or prostaglandin $E_2$. The disadvantages of non-specific inhibition of prostaglandin $E_2$ and high pharmacologically effective molar concentrations associated with the use of enzyme inhibitors, such as indomethacin and indomethacin-like analogs are therefore avoided. The methods may be used for regulating the production of vasoconstrictive prostanoids from chorionic tissues, such as the amnion, the chorion, the placenta or the decidua. In addition, analogs of IGF-I and IGF-II are anticipated to provide the specific prostanoid regulation from chorionic tissues in conjunction with the claimed invention.

In one aspect of the present invention, a method for selectively regulating chorionic cell, particularly placental cell, production of thromboxane and prostaglandin $F_{2\alpha}$ is provided. The method most preferably comprises treating placental cells with a pharmacologically effective amount of insulin-like growth factor (IGF-I) or an analog thereof. For purposes of describing the present invention, a pharmacologically acceptable concentration of IGF-I is defined as an amount sufficient to inhibit thromboxane and prostaglandin $F_{2\alpha}$ production by placental cells without inhibiting placental prostaglandin $E_2$ or prostacyclin ($PGI_2$) production. While inhibition of thromboxane and prostaglandin $F_{2\alpha}$ production will occur upon treatment with IGF-I, production of prostaglandin $E_2$, human chorionic gonadotropin and PGFM will remain unaffected.

It is expected that either IGF-I, IGF-II, or analogs of these agents, may be employed in the described methods. However, IGF-I is most preferred. The described method may be employed to regulate production of chorionic thromboxane and $PGF_{2\alpha}$ in any variety of normal or abnormal placental cells, such as those of farm or domesticated animals or humans. In a most preferred embodiment, the claimed method provides for the regulation of human chorionic tissue prostanoid production, particularly by human placental cells. In an even more preferred embodiment, the human placental cells are defective in uterine blood flow as observed in IUGR placentas.

In this particular aspect of the invention, a pharmacologically effective concentration of insulin-like growth factor, particularly IGF-I, effective to inhibit thromboxane production by human placental cells in vivo is defined as an amount sufficient to achieve a concentration of between about $10^{-7}$ to about $10^{-10}$ M. This amount constitutes a pharmacologically active dose that is well within physiological ranges, and therefore can be readily used by the artisan of ordinary skill in pharmacy as a basis for defining an appropriate dose to be used in vivo as part of an appropriate human dose regimen.

A further embodiment of the invention is a method for treating hypertension in a pregnant animal. The method comprises administering a pharmacologically effective concentration of insulin-like growth factor to inhibit thromboxane and prostaglandin $F_{2\alpha}$ production without inhibiting prostaglandin $E_2$ or prostacyclin production. The insulin-like growth factor may be IGF-I, IGF-II, or an analog thereof. In a preferred embodiment, the insulin-like growth factor is IGF-I and the animal is a human. Preferably, the production of human chorionic gonadotropin and PGFM is unaffected. The pharmacologically effective concentration of insulin-like growth factor is between about $10^{-7}$ to about $10^{-10}$ M, and the factor may be administered subcutaneously, intramuscularly, intravenously or intra-amniotically in a pharmacologically acceptable carrier solution.

Another embodiment of the invention is a method for treating intrauterine growth retardation in a pregnant animal. The method comprises administering a pharmacologically effective concentration of insulin-like growth factor to inhibit thromboxane production by placental cells without inhibiting prostacyclin production as described hereinabove.

A method for preventing a fetus from growing to an abnormally large size is a further embodiment of the invention. The method comprises administering a pharmacologically effective amount of an inhibitor of insulin-like growth factor to an animal pregnant with the fetus, wherein prostacyclin, $PGE_2$, PGFM and human chorionic gonadotropin production is not inhibited. The inhibitor of insulin-like growth factor may be an antibody having specific binding affinity for insulin-like growth factor I, and the antibody is, preferably, a monoclonal antibody. In a preferred embodiment, the fetus is a human fetus. The inhibitor of insulin-like growth factor may be administered subcutaneously, intramuscularly intravenously, or intra-amniotically; and may be an antagonist of insulin-like growth factor I, or a metabolizing enzyme of insulin-like growth factor I. This method may be particularly applicable to gestational diabetes where increased growth of the baby is frequently associated with gestational diabetes.

In still another embodiment of the invention, a method for inhibiting labor by inhibiting the production of thromboxane and prostaglandin $F_{2\alpha}$ by placental cells is provided. The method most preferably comprises administering to a pregnant animal a pharmacologically effective amount of insulin-like growth factor sufficient to inhibit the production of thromboxane ($TxB_2$) and prostaglandin $F_{2\alpha}$ by chorionic cells without affecting prostacyclin, prostaglandin $E_2$, PGFM, and human chorionic gonadotropin (hCG) production.

The present invention also provides methods for regulating vasoconstriction through the administration of insulin-like growth factor, such as IGF-I or IGF-II, or analogs thereof. IGF-I is most particularly preferred for this use. This method would be particularly efficacious for the treatment of IUGR or pregnancy-induced hypertension in a pregnant animal. Again, the specific inhibitory activity of IGF-I on placental tissue production of vasoactive prostanoids, such as thromboxane and prostaglandin $F_{2\alpha}$, provides a potentially powerful clinical tool in the management of this pathology without the undesirable side effects associated with other non-specific prostanoid inhibitors.

While the claimed method may be useful in the treatment of any variety of animals, the present inventor contemplates that the particular utility of the method is in the treatment of pregnancy-induced hypertension, premature labor, or IUGR in humans.

For premature labor, spontaneous labor prior to between about 20 and about 34 weeks gestation in a pregnant human female may be inhibited employing the present method by administering a pharmacologically effective dose of a clinical grade insulin-like growth factor I (IGF-I) to the patient. Clinical grade insulin-like growth factor (IGF-I or IGF-II), particularly IGF-I and IGF-II made by recombinant techniques are available from pharmaceutical suppliers, such as for human use. The dose of insulin-like growth factor to be administered to the patient will vary depending upon the particular circumstances of the patient being treated, for example, the mode or delivery (vaginal, C-section), the weight of the pregnant female, and the particular gestational age of the fetus. The IGF-I or IGF-II would be given to the patient until clinical indications of the labor subsiding, such as cessation of contractions or halted cervical dilation and effacement is observed by the attending physician. These parameters are well known to those of skill in the obstetrical arts, as is the determination of appropriate doses to administer to a patient given the disclosure provided herein.

For treatment of pregnancy-induced hypertension or IUGR, a pharmacologically effective dose of a clinical grade IGF-I may be administered to the patient at any time during pregnancy, after IUGR has been diagnosed. The dose of insulin-like growth factor to be administered to the patient will vary depending upon the particular circumstances of the patient being treated, for example, the degree of hypertension, the weight of the fetus, and the particular gestational age of the fetus. The IGF-I or IGF-II would be given to the patient until clinical indications of pregnancy-induced hypertension or IUGR subside, such as improved uteroplacental blood flow or promotion of intrauterine growth. These parameters are known to those of skill in the obstetrical arts, as is the determination of appropriate doses to administer to a patient given the disclosure provided herein.

It is contemplated that a pharmacologically effective amount of insulin-like growth factor, IGF-I, sufficient to inhibit thromboxane production by placenta in a pregnant human female will generally be an amount sufficient to achieve a concentration of between about $10^{-7}$ to about $10^{-10}$ M in the amniotic fluid surrounding the fetus or umbilical cord blood of the fetus. Insulin-like growth factor may be administered to the patient by any variety of routes, for example, subcutaneously, intramuscularly, intravenously, or intra-amniotically. Most preferably, the insulin-like growth factor is to be administered to the patient intra-amniotically. The insulin-like growth factor-I (IGF-I) may be administered to the patient as it is obtained from the pharmaceutical supplier in a pharmaceutically acceptable carrier solution, or may be diluted to a desired dosage with pharmaceutically acceptable carrier solutions generally available from pharmaceutical suppliers. Clinical grade preparations of IGF-I and IGF-II are available for use in humans in conjunction with the practice of the present invention.

The present disclosure also provides a method for inducing labor in a pregnant animal. According to one embodiment of the method, labor is to be induced by inhibiting IGF-I in the animal, which would be expected to result in a concomitant increase in the production of thromboxane and $PGF_{2\alpha}$ from chorionic tissues, particularly placental cells. The present inventor contemplates that these physiological events may be accomplished by administering a pharmacologically effective amount of a specific inhibitor of insulin-like growth factor-I (IGF-I) or insulin-like growth factor-II (IGF-II) to the pregnant animal.

By way of example, specific inhibitors of insulin-like growth factor IGF-I or IGF-II include antibodies having specific binding affinity for IGF-I or IGF-II. While both polyclonal and monoclonal antibodies may be employed for such use, monoclonal antibodies are most preferred. By way of example, a monoclonal antibody specific for IGF-I may be prepared according to standard hybridoma preparation techniques as outlined in the present disclosure. Other specific inhibitors of insulin-like growth factor that are contemplated by the present inventor to be useful in the described method for inducing labor include synthetic antagonists of IGF-I or IGF-II, and metabolizing enzymes of IGF-I or IGF-II. Specific inhibitors of IGF-I may be administered to an animal through any variety of routes, including subcutaneous, intramuscular, or intravenous administration, as described above.

In practice, the attending physician would administer an inhibitor of insulin-like growth factor (such as IGF-I, IGF-II) to a pregnant female of at least 40 weeks gestational age, or to a female of lesser gestational age medically where indicated, and continue to administer the IGF-I or IGF-II inhibitor until clinically recognized symptoms of the onset of labor are observed, such as the onset of contractions or dilation of the cervix effacement.

It is anticipated that the described method may be particular efficacious in the treatment of pregnant human females having progressed beyond about 42 weeks gestational age, or in those situations where the induction of labor is otherwise medically indicated for the safety of the mother and/or child. Again, the specific inhibitor of insulin-like growth factor would be administered to the pregnant female until contractions commence and/or until the observation of other clinically recognized signs of labor onset, such as dilation of the cervix or effacement.

Standard gynecological and obstetrical clinical procedures well known to those of skill in the obstetrical art would be employed in the application of the herein disclosed methods for both inhibiting and inducing labor, as well as in the treatment of pregnancy-induced hypertension or abnormal fetal growth, given the present disclosure of the specific activity of the insulin-like growth factor I on human placental cells, and the specific inhibitory effect that IGF-I and IGF-II inhibitors are anticipated to have on chorionic tissue prostanoid production.

The present inventor envisions that antagonists of insulin-like growth factor that increase thromboxane levels would be useful for the converse of the conditions where an agonist inhibits thromboxane levels. For example, a method of treating hypotension may comprise the administration of a pharmacologically effective concentration of an antagonist of insulin-like growth factor.

The following abbreviations are employed throughout the description of the present invention:
DMSO=Dimethyl sulfoxide
hCG=human Chorionic Gonadotrophin $PGE_2$=prostaglandin $E_2$
6-Keto-$PGF_{1\alpha}$=6-keto prostaglandin $F_{1\alpha}$
PGFM=13, 14, -dihydro-15 keto-prostaglandin $F_2$
BSA=Bovine serum albumin
EDTA=ethylene diamine tetraacetic acid
U=Units
$TxB_2$=Thromboxane $B_2$
IGF-I=Insulin-like growth factor-I
$PGF_{2\alpha}$=prostaglandin $F_{2\alpha}$
$PGI_2$=prostacyclin
PGA=prostaglandin A
PIH=pregnancy-induced hypertension
GnRH=Gonadotrophin releasing hormone
NDGA=Nordihydroguaiaretic Acid

DETAILED DESCRIPTION OF THE PREFERRED EMBODIMENTS

Figure 1:
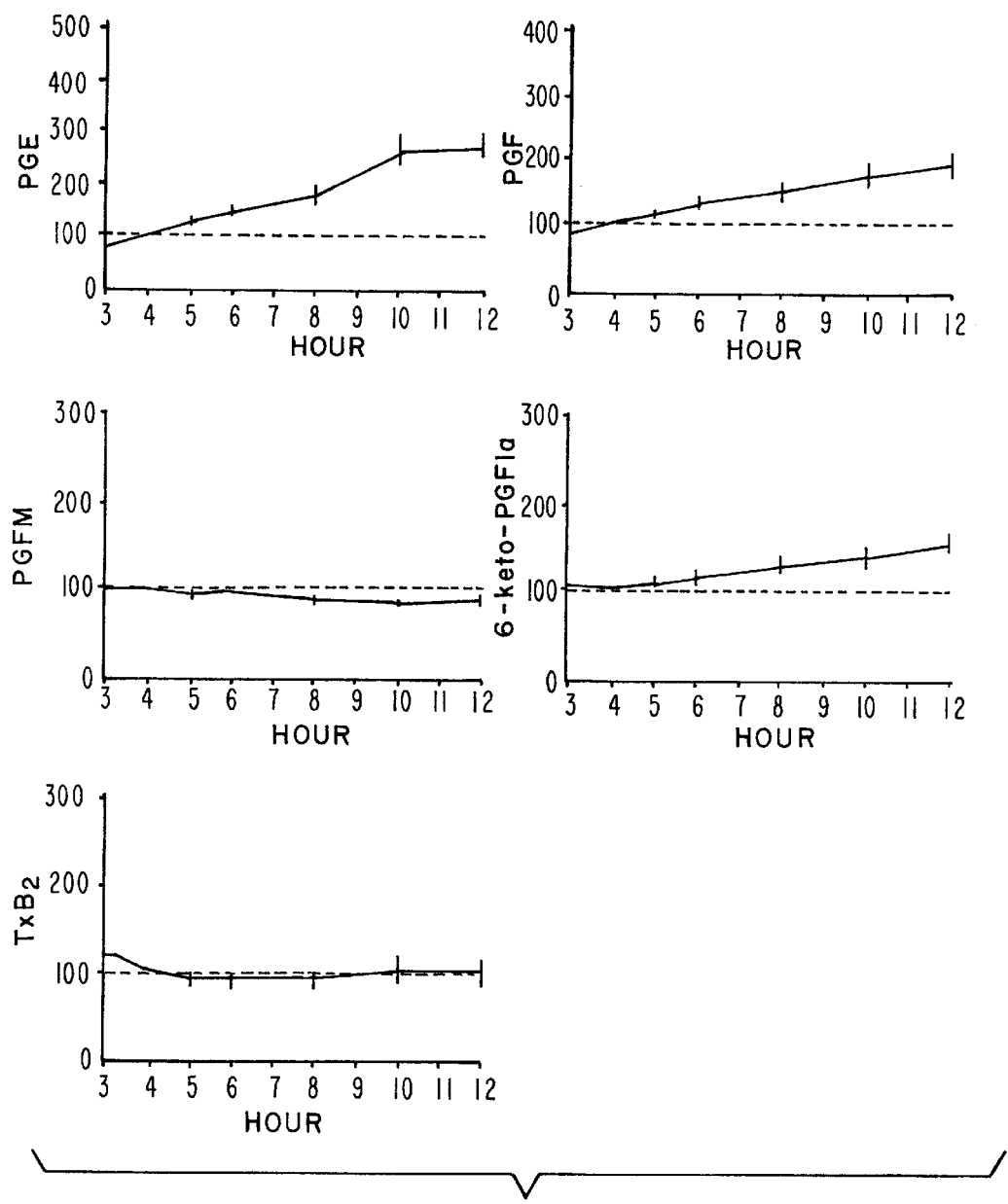
FIG. 1. Basal prostanoid release, normalized to the fourth hour release, of PGE, $PGF_{2\alpha}$, PGFM, 6-keto-$PGF_{1\alpha}$ and $TxB_2$ from human term placenta (mean±SEM).

Methods for selectively regulating the production of prostanoids from chorionic tissues, particularly placental tissue are provided. Chorionic production of thromboxane $B_2$ and prostaglandin $F_{2\alpha}$ is regulated (inhibited) without significant effects on prostaglandin $E_2$ or prostacyclin production by placental cells by administering a pharmacologically effective dose of IGF-I, IGF-II, or analog thereof. The methods also include improved strategies for treating abnormal pregnancies such as pregnancy-induced hypertension or IUGR or for managing premature labor by use of IGF-I, IGF-II, or analogs thereof and for treating abnormal pregnancies such as IUGR. Techniques for inducing labor in an animal are also provided by decreasing IGF-I in an animal, by, for example, administering a specific inhibitor of IGF-I or IGF-II.

Amounts of prostacyclin ($PGI_2$) were determined as a measure of 6-keto-$PGF_{1\alpha}$. 6-keto-$PGF_{1\alpha}$ is the immediately formed metabolite of the active molecule $PGI_2$ (see FIG. 7A and FIG. 7B), and thus provides an accurate measure of $PGI_2$ amounts.

Amounts of thromboxane A were determined as a measure of thromboxane $B_2$. Thromboxane A is converted almost instantaneously to thromboxane $B_2$, and therefore constitutes a well accepted measure of thromboxane $B_2$ by those of ordinary skill in the art.

Recombinant IGF-I was purchased from Chemicon International, Inc. (Terecula, Calif.). Clinical grade IGF-I may be obtained from Chemicon International, Inc., Terecula, Calif., that sells a recombinant form of IGF-I that may be formulated according to standard pharmaceutical techniques to provide a preparation particularly suitable.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are presented to describe preferred embodiments and utilities of the present invention, but should not be construed as limiting the claims thereof.

EXAMPLE 1

RADIOIMMUNOASSAYS

The present example describes the various assays and materials used by the inventor in the characterization of chorionic, particularly placental, tissue response.

Prostanoid Radioimmunoassays

Radioimmunoassays were performed in a fashion similar to what has been previously described (Siler-Khodr et al., 1986b) which is specifically incorporated herein for this purpose, with specific exception as noted below. A perifusion model (described in Examples 2) was employed to determine placental cell response. Media collected from the perifusion samples prepared from placental tissues were assayed. After an initial pilot study of the prostanoid release of each of the perifusion placental tissue media samples collected hourly, samples from hours 3, 4, 5, 6, 8 and 12 of the perifusion were chosen for assay and for data analysis. All the samples from a given perifusion (placenta) were determined in the same assay.

PGE—A specific antiserum for PGE (both 1 and 2, 50% and 100%, respectively) obtained from Advanced Magnetics, Inc. (Cambridge, Mass.) was used at a final dilution of 1/37,500. Label [5,6,8,11,12,14,15(n)-$^3$H]-PGE$_2$, which was purchased from Amersham Corp. (Arlington Heights, Ill.), was added to every tube (25 pg). Assay sensitivity was 8 pg/tube and the intra- and interassay coefficients of variation were 7.8% and 9.8%, respectively. The only cross-reactivities greater than 1% were PGA$_2$, 6%; PGA$_1$, 30%; and PGF$_{2\alpha}$, 1.3%.

PGF$_{2\alpha}$—A specific antiserum for PGF$_{2\alpha}$ prostaglandins obtained from Advanced Magnetics, Inc. was used at a final dilution of 1/60,000. Label [5,6,8,9,11,12,14,15(n)-$^3$H]-PGF$_{2\alpha}$, which was purchased from Amersham Corp., was added to every tube (25 pg). Assay sensitivity was 1.5 pg/tube and the intra- and interassay coefficients of variation were 11.0% and 10.4%, respectively. The only cross-reactivities greater than 0.1% were PGE$_1$, 1.1%, 6-keto-PGF$_1$, 1.1%; TxB$_2$, 0.5%; and PGE$_2$, 0.3%.

PGFM—A specific antiserum to PGFM was obtained from Advanced Magnetic, Inc. and used at a final dilution of 1/4,000. Label [5,6,8,9,11,12,14(n)-$^3$H]-13,14-dihydro-15-keto-PGF$_{2\alpha}$, which was purchased from Amersham Corp., was added to every tube (25 pg). Assay sensitivity was 7 pg/tube and the intra- and interassay coefficients of variation were 10.2% and 9.6%, respectively. The only cross-reactivities greater than 0.1% were PGF$_{2\alpha}$, 1.7% and 13,14-dihydro-15-keto-PGE$_2$, 0.14%.

TxB$_2$—A specific antiserum to TxB$_2$ was obtained from Advanced Magnetic, Inc. (Cambridge, Mass.) and used at a final dilution of 1/70,000. Label [5,6,8,9,11,12,14(n)-$^3$H]-TxB$_2$, which was purchased from Amersham Corp. (Arlington Heights, Ill.), was added to every tube (25 pg). Alternatively label I-125-TxB$_2$, purchased from Advanced Magnetic, Inc., was added to every tube (4000 cpm). Assay sensitivity was 1.7 pg/tube and the intra- and interassay coefficients of variation were 5.3% and 5.7%, respectively. There were no cross-reactivities greater than 0.1%.

6-Keto-PGF$_{1\alpha}$—A specific antiserum to 6-keto-PGF$_{1\alpha}$ was obtained from Advanced Magnetics, Inc. and used at a final dilution of 1/137,500. Label [5,6,8,9,11,12,14(n)-$^3$H]-6-keto-PFG$_{1\alpha}$, which was purchased from Amersham Corp. (Arlington Heights, Ill.), was added to every tube (25 pg). Assay sensitivity was 7 pg/tube and the intra- and interassay coefficients of variation were 8.6% and 7.4%, respectively. The only cross-reactivities greater than 0.01% were PGF$_{1\alpha}$, 7.8%, 6-keto-PGE$_1$, 6.8%; PGF$_{2\alpha}$, 2.2%; PGE$_1$, 0.7%; PGE$_2$, 0.6%.

hCG—A specific antiserum to hCG was obtained from Advanced Magnetic, Inc. and used at a final dilution of 1/500,000. Radio-iodinated hCG (CR-119) (500 pg) having a specific activity of 350 $\mu$Ci/$\mu$g was added to every tube. Assay sensitivity was 1.7 pg/tube and the intra- and interassay coefficients of variation were 5.3% and 5.7%, respectively. There were no cross-reactivities greater than 0.1%.

Prostanoid Recovery and Stability

Samples were stored at –20° C. until assayed for PGE, PGF$_{2\alpha}$, PGFM, TxB$_2$, 6-keto-PGF$_{1\alpha}$ and hCG. Recovery and stability of these prostanoids in the perifusion system used in the present studies and during storage was assessed by spiking the medium with prostanoids and perifusing it through empty chambers and collecting samples as described above. In addition, samples were frozen and thawed repeatedly and re-assayed.

Prostanoid recovery and stability in the systems described illustrating the present invention were nearly 100%. PGE, PGF$_{2\alpha}$, PGFM, TXB$_2$, 6-keto-PGF$_{1\alpha}$ and hCG were obtained from the sources previously described herein, as well as characterized in and between assays as described.

EXAMPLE 2

EFFECT OF ENZYME INHIBITORS ON PLACENTAL PROSTANOID RELEASE

A perifusion system was employed to investigate the release of prostaglandin E$_2$ (PGE), prostaglandin F (PGF$_{2\alpha}$), PGFM and the stable metabolites of thromboxane A$_2$ (TxB$_2$) and PGI$_2$, i.e., thromboxane B$_2$ (TxB$_2$) and 6-keto-prostaglandin F$_{1\alpha}$ (6-keto-PGF$_{1\alpha}$) from human term placentas. The effect of increased availability of arachidonic acid (Example 3) and inhibitors of arachidonic acid metabolism, such as quinacrine, and of enzyme inhibitors, such as EDTA, nordihydroguaiaretic acid (NDGA) and indomethacin (Example 2), was compared to basal placental prostanoid release. These studies provide new data relating to rate-limiting steps in the basal release of prostanoids from the human term placenta. Radioimmunoassay was conducted as described in Example 1.

A. MATERIALS AND METHODS

1. Materials

Medium 199 (x2) with Earles' Modified Salts, bicarbonate and L-glutamine without phenol red was purchased from Gibco Laboratories (Chargin Falls, Ohio). Penicillin, streptomycin, BSA, estradiol, progesterone and dexamethasone were obtained from Sigma Chemicals (St. Louis, Mo.). Quinacrine, NDGA, EDTA and indomethacin were also purchased from Sigma Chemicals. Arachidonic acid was obtained from Sigma Chemicals by overnight mail and used within one week of receipt. IGF-I was purchased from Chemicon International, Inc. (Terecula, Calif.).

2. Placental Perifusion

Term placentas were obtained and placed on ice immediately after vaginal delivery from patients having spontaneous labor and delivery without any known obstetrical or medical complications. Tissues were obtained in accordance with a protocol approved by the Institutional Review Board. Within 30 minutes, the placental tissues were dissected of decidua, chorionic plates and large fetal vessels on ice. The placental tissues were cut into small fragments (approximately 25 pieces having a total weight of approximately 1 g), rinsed free of blood by repeated washing with ice cold normal saline until clear in color, and the tissue fragments placed in a 3-ml tissue chamber, placed in a 37° C. water bath. Twenty replicate chambers were prepared and each perifused with Medium 199 containing 0.05% BSA, 100 U penicillin and 100 $\mu$g streptomycin per ml at a rate of 1 ml per hour for 12 hours. This medium is hereafter in this Example, referred to as Medium 199. The influx medium was aerated with 95% air and 5% $CO_2$ throughout the perifusion. Perifusion was performed for two hours prior to initiation of sample collection. In this fashion, all tissues were thoroughly washed and equilibrated. Samples were collected hourly, beginning at the start of the third hour, into 12×75 mm glass tubes containing 0.1 ml indomethacin and 1100 $\mu$g/ml dimethyl sulfoxide [DMSO]. It took approximately one hour for the input medium to pass through the perifusion tubing and chamber and to be collected in the sample tube, thus the dead volume of the system was approximately 1 ml. Collection of the effluent of the 20 chambers was done simultaneously, using an ISCO fraction collector Retriever III adapted with a 20-tube rack and manifold.

3. Enzyme Inhibitor Procedure

At the beginning of the fifth hour of the perifusion, Medium 199 in the experimental chambers was changed to Medium 199 containing quinacrine (10 $\mu$M), EDTA (1 mM), NDGA (10 $\mu$M) or indomethacin (50 $\mu$g/ml). Four replicated chambers were perifused with control medium and each of the experimental media. This experimental design was repeated in three different perifusions using placental tissues from three different patients according to the procedure described in Example 3. Incubation with indomethacin resulted in an immediate inhibition of PG, $PGF_{2\alpha}$, $TxB_2$ and 6-keto-$PGF_{1\alpha}$, with a delayed inhibition of PGFM.

4. Statistical Analysis

The prostanoid release for a given chamber was expressed as the increase over the fourth-hour prostanoid release for that chamber. Because there may be differences in the amounts of blood vessels and connective tissue among placental explants, the release expressed per unit weight results in high variance between chambers. On the other hand, it was observed that expressing each chamber's response in relation to its initial release resulted in a very low variance between replicate chambers. Thus, the release of each chamber was related to its functional competence at the time of treatment rather than its mass.

The mean release for replicate chambers from a given placenta for each particular prostanoid in the presence of each of the various enzyme inhibitors or arachidonic acid (Example 3) was calculated and then the mean data for each of the three different placentas was averaged at each time point. Thus, each placenta was weighted equally in the statistical analyses. Two-way analysis of variance of the average response for each prostanoid for each enzyme inhibitor studied or each dose of arachidonic acid (Example 3), at each time point, was performed. The normalized data were tested for homogeneity using Cohrna's Q test, and no significant deviation was found. Thus, for each prostanoid and each treatment, where there was a significant main effect or interaction, Dunnen's comparison test was applied to determine the point(s) of significant difference as compared to the control. $P<0.05$ was considered to be statistically significant.

B. RESULTS

1. Basal Placental Prostanoid Release

The basal (control) release (mean±SEM) of PGE, $PGF_{2\alpha}$, PGFM, 6-Keto-$PGF_{1\alpha}$, and $TxB_2$ per mg wet weight of tissue from seven placentas, from the third to the 12th hour of perifusion, is given in Table 1. The coefficient of variation within and between placentas was as much as 40% when release rate per mg of tissue was analyzed. However, if the release in a given perifusion chamber is normalized to the fourth-hour release for that chamber, and the mean of the four replicate chambers of each given placenta then determined, the variation between chambers for the given placenta is very small.

In addition, the release patterns between different placentas have an average coefficient of variation of only 25%, 21%, 13%, 16%, and 25%, for PGE, $PGF_{2\alpha}$, PGFM, 6-keto-$PGF_{1\alpha}$ and $TxB_2$, respectively, over the perifusion period. FIG. 1 illustrates the average normalized release patterns (mean±SEM) for these prostanoids from the control chambers of seven different placentas over the perifusion period. In the case of PGE, $PGF_{2\alpha}$ and 6-keto-$PGF_{1\alpha}$ the rate of release increased significantly (from the fourth to the sixth hour for PGE, from the fourth to the 12th hour normalized releases of PGFM and $TxB_2$ were relatively constant throughout this perifusion period. As can be seen in FIG. 1, the greatest variance is seen in the later hours of the perifusion with relatively small variance between placentas in the earlier perifusion hours, using the fourth-hour normalized data.

TABLE 1

The basal release (mean ± SEM) of PGE, $PGF_{2\alpha}$, PGFM; 6-keto-$PGF_{1\alpha}$ and $TxB_2$ expressed as pg per mg wet weight of tissue from seven term placentas during 12 hours of perifusion

| | PGE | | $PGF_{2\alpha}$ | | PGFM | | 6-keto-$PGF_{1\alpha}$ | | $TxB_2$ | |
| --- | --- | --- | --- | --- | --- | --- | --- | --- | --- | --- |
| HOUR | (pg/) | mean ± SEM | (pg/) | mean ± SEM | (pg/) | mean ± SEM | (pg/) | mean ± SEM | (pg/) | mean ± SEM |
| 3 | 1043 | 260 | 949 | 141 | 2751 | 254 | 254 | 33 | 6017 | 1284 |
| 4 | 1200 | 285 | 1198 | 165 | 2876 | 242 | 242 | 36 | 4944 | 920 |
| 5 | 1391 | 258 | 1331 | 161 | 2581 | 270 | 254 | 40 | 4348 | 696 |
| 6 | 1704 | 364 | 1534 | 176 | 2808 | 259 | 264 | 34 | 4195 | 592 |
| 8 | 1958 | 301 | 1787 | 233 | 2508 | 282 | 390 | 50 | 4234 | 596 |

TABLE 1-continued

The basal release (mean ± SEM) of PGE, $PGF_{2\alpha}$, PGFM; 6-keto-$PGF_{1\alpha}$ and $TxB_2$ expressed as pg per mg wet weight of tissue from seven term placentas during 12 hours of perifusion

| | PGE | | $PGF_{2\alpha}$ | | PGFM | | 6-keto-$PGF_{1\alpha}$ | | $TxB_2$ | |
|---|---|---|---|---|---|---|---|---|---|---|
| HOUR | (pg/) | mean ± SEM | (pg/) | mean ± SEM | (pg/) | mean ± SEM | (pg/) | mean ± SEM | (pg/) | mean ± SEM |
| 10 | 2266 | 235 | 1930 | 253 | 2209 | 190 | 286 | 39 | 4328 | 720 |
| 12 | 3181 | 434 | 2288 | 292 | 2428 | 296 | 383 | 66 | 4474 | 599 |

2. Placental Prostanoid Release in the Presence of Enzyme Inhibitors

FIG. 2A, FIG. 2B, FIG. 2C and FIG. 2D illustrates the percent response over the control release for each hormone for each enzyme inhibitor studied. Significantly different responses for each prostanoid, comparing the various treatment over time to the controls using two-way analysis of variance, were noted. Points of significant difference were determined, using the mean normalized response of the three different placentas for each prostanoid studied.

Figure 2:
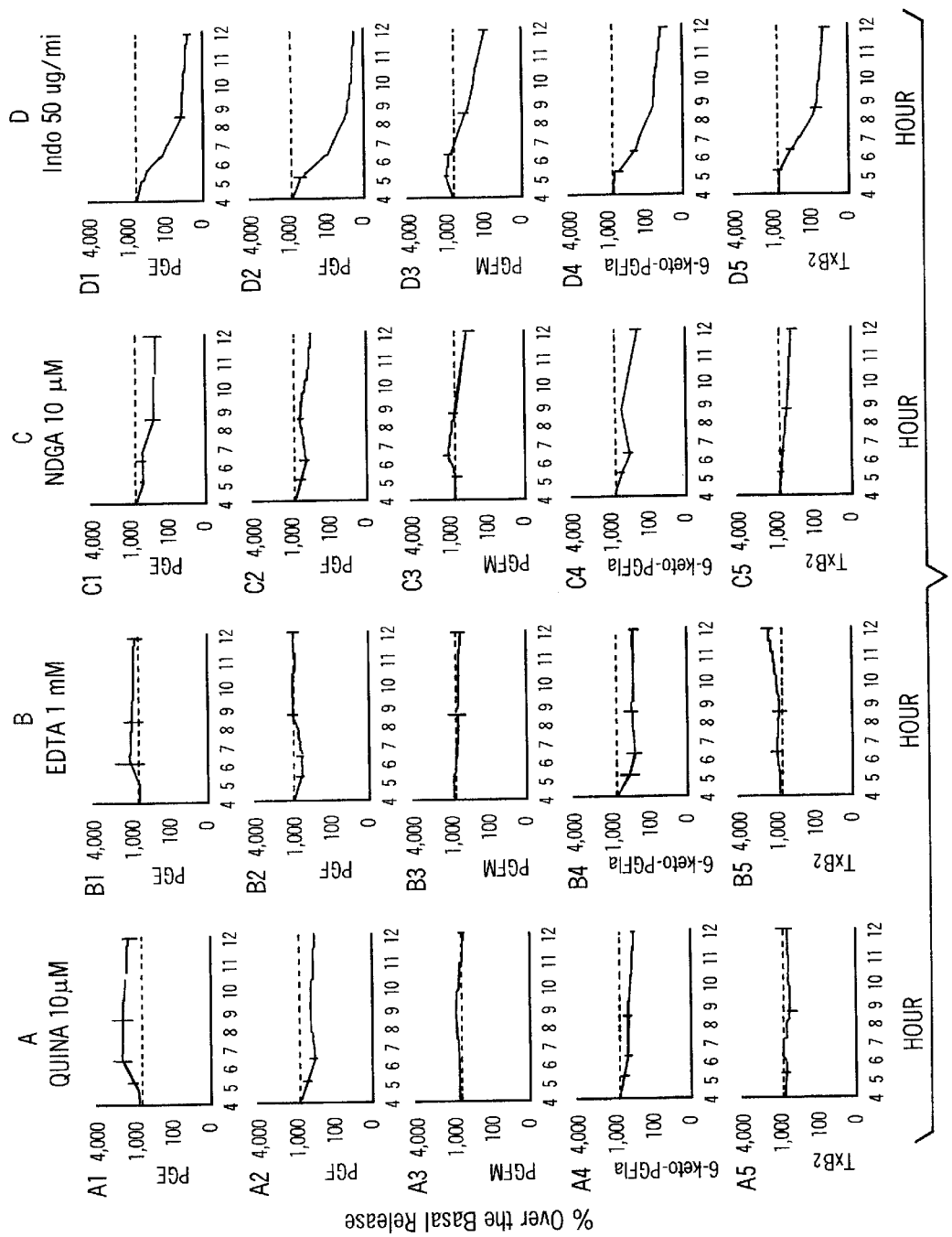
FIG. 2A. Effect of eiconasoid enzyme inhibitor quinacrine on percent release over the control (mean±SEM) of PGE, $PGF_{2\alpha}$, PGFM, 6-keto-$PGF_{1\alpha}$ and $TxB_2$ from human term placenta.
FIG. 2B. Effect of eiconasoid enzyme inhibitor EDTA on percent release over the control (mean±SEM) of PGE, $PGF_{2\alpha}$, PGFM, 6-keto-$PGF_{1\alpha}$ and $TxB_2$ from human term placenta.
FIG. 2C. Effect of eiconasoid enzyme inhibitor NDGA on percent release over the control (mean±SEM) of PGE, $PGF_{2\alpha}$, PGFM, 6-keto-$PGF_{1\alpha}$ and $TxB_2$ from human term placenta.
FIG. 2D. Effect of eiconasoid enzyme inhibitor indomethacin on percent release over the control (mean±SEM) of PGE, $PGF_{2\alpha}$, PGFM, 6-keto-$PGF_{1\alpha}$ and $TxB_2$ from human term placenta.

The addition of 10 μM of quinacrine to the perifusion medium had no significant effect on the release of PGE, PGFM, 6-keto-$PGF_{1\alpha}$ or $TxB_2$ from term placental explants (FIG. 2A). For $PGF_{2\alpha}$, there was a significant inhibition of its release during the first hour of quinacrine exposure. Thereafter, the $PGF_{2\alpha}$ release remained less than controls, but this reduction was not significant.

The addition of 1 mM EDTA (FIG. 2B) or NDGA (FIG. 2C) resulted in a significant inhibition of 6-keto-$PGF_{1\alpha}$. The inhibition was significant within the first hour of tissue exposure and was sustained throughout the perifusion period.

The addition of indomethacin (50 μg/ml) (FIG. 2D) to the perifusion medium resulted in a rapid inhibition of PGE, $PGF_{2\alpha}$, 6-keto-$PGF_{1\alpha}$ and $TxB_2$ release from these placental explants, i.e., 33.5, 22.1, 41.3 and 42.3% of control, respectively, at three hours post-exposure. Continued perifusion with indomethacin inhibited these prostanoid releases to 24.0%, 9.6%, 26.3%, and 30.5% of the control, respectively, yet detectable levels were still observed. Interestingly, the PGFM release from these placental explants was not inhibited by indomethacin even after three hours of exposure. However, after seven hours of perifusion, indomethacin inhibited PGFM release to 51.8% of the release from the control placental explant cultures.

Quinacrine had little if any significant effect on the release of these prostanoids. Arachidonate may therefore be liberated by phospholipase $A_2$ and may not be rate-limiting in the human term placenta for these prostanoid releases.

Similarly, $Ca^{++}$ chelator which inhibits phospholipase C activity, also did not reduce PGE, PGFM or $TxB_2$ production. The lack of effect of EDTA in these studies may be due to changes in extra-cellular $Ca^{++}$ that did not influence the intra-cellular $Ca^{++}$. However, previous studies by Olson et al. (1983a) have observed an inhibitory action of low extra-cellular $Ca^{++}$ on amnion prostanoid release. A significant inhibition of the already low release of 6-keto-$PGF_{1\alpha}$ was observed in the present studies. Thus, the synthesis of $PGI_2$ by prostacyclin synthetase should be $Ca^{++}$-dependent, and the low extra-cellular $Ca^{++}$ milieu should have been translated intra-cellularly. The present data may suggest that increasing $Ca^{++}$ may stimulate prostacyclin release and may also be a means of regulating prostacyclin production.

The addition of NDGA to the medium which inhibited PGE as well as 6-keto-$PGF_{1\alpha}$ (FIG. 2C) may indicate a regulation at the level of endoperoxide isomerase and prostacyclin synthetase. Previous studies in the hypothalamus (Negro-Vilar et al., 1986) observed no inhibition of PGE in the presence of NDGA. They also noted an increase in GnRH release. The present inventor has demonstrated that GNRH may inhibit prostanoid release from human term placental tissue; thus, the actions of NDGA observed herein may be effected via chorionic GnRH. NDGA also reduced leukotrienes.

The reduction of placental PGE, $PGF_{2\alpha}$, 6-keto-$PGF_{1\alpha}$ and $TxB_2$ by indomethacin confirms the activity of the placental cyclooxygenase in these prostanoid releases. Interestingly, a significant inhibition of PGFM release was observed only many hours after incubation with indomethacin, thus indicating that the enzyme(s) metabolizing $PGF_{2\alpha}$ to PGFM were saturated with substrate in the term placenta and only after reduction of $PGF_{2\alpha}$ production and/or induction of metabolizing enzyme(s), was PGFM release significantly reduced. Observation of the basal release of $PGF_{2\alpha}$ and PGFM also supports this finding. $PGF_{2\alpha}$ increases nearly three fold from the fourth to the twelfth hour of perifusion, yet PGFM is constant. This again indicates that the placental enzyme(s) metabolizing $PGF_{2\alpha}$ to PGFM should be saturated, such that further PGFM release could not occur. These findings differ from previous predictions based on demonstration of the very high activity of metabolizing enzyme in the placenta and the significant metabolism of PGE (Myatt, 1990). However, the activity of PGDH for $PGF_{2\alpha}$ is one-sixth that for PGE (Jarabak, 1972). Thus, $PGF_{2\alpha}$ metabolism may be saturated, whereas PGE is not. This may be of physiologic significance, as an increase in cyclooxygenase activity would then lead to an increase in $PGF_{2\alpha}$ without an increase in PGE.

A comparison of the relative ratio of prostanoid release as reported in the present disclosure demonstrates $TxB_2$ to be produced in the highest amounts. In the system employed in the present studies, the relative release of $PGF_{2\alpha}$ to its metabolite was greater than that observed by Mitchell et al. (1978c) or Olson et al. (1983c). On the other hand, production of 6-keto-$PGF_{1\alpha}$ was less, probably due to the use of 95% air in the present system rather than 95% $O_2$ which is known to reduce $PGI_2$ production (Ekblad et al., 1987). Because the present studies sought to emulate a physiologic system, 95% air:5% $CO_2$ was employed in the study in vitro system. This aeration resulted in an $O_2$ partial pressure of 100–150 mm Hg, which is a physiologic level in the human term placenta.

Of interest is the striking increase in the basal release for PGE, $PGF_{2\alpha}$ and 6-keto-$PGF_{1\alpha}$ during the fourth to the twelfth hours using this culture system (see Table 1).

It has been suggested previously that high $TxB_2$ release reflects blood contamination of the tissue (Myatt, 1990). However, in the present studies, the tissue was washed for hours and the initially very high $TxB_2$ release declined over the first three to four hours, persisted at high levels, and then increased again by the 12th hour of perifusion. Thus, the release of $TxB_2$ observed herein from the fifth hour on is indeed due to trophoblastic function.

These studies demonstrate the high biosynthetic competence of the human placenta for prostanoid production. These studies provide a reference for mean production because human placental explants were used. Based on the data provided in the present study a term size placental tissue is estimated to produce greater than 4,000 ng/hour of these five prostanoids alone. The function of the placenta is hypothesized to be both endocrine and paracrine due to its vasculature and its intra-uterine position. These factors, together with the teachings of the present disclosure, are used in the definition of the herein disclosed methods to regulate chorionic prostanoid production to affect uterine, fetal and intra-uterine function in the management of labor.

EXAMPLE 3

EFFECT OF ARACHIDONIC ACID ON PLACENTAL PROSTANOID RELEASE

Prostaglandins and prostanoids, including prostacyclin, thromboxane $A_2$, and the leukotrienes, are formed from certain polyunsaturated fatty acids, principally arachidonic acid. The present example demonstrates that prostanoid production by the human placenta is not limited by arachidonic acid availability.

A. MATERIALS AND METHODS

All materials and methods were as described in Examples 1 and 2. The effect of exogenous arachidonic acid on basal prostanoid release was studied by perifusing placental tissue from the beginning of the fifth hour of the perifusion, with Medium 199 containing arachidonic acid (0.2, 1.0 or 10 μg/ml). Arachidonic acid was dissolved in ethanol such that 0.02 ml ethanol per 100 ml of Medium 199 was needed to obtain these concentrations, and the resulting ethanol concentration was 0.02%. The control medium was also made to be 0.02% ethanol for valid comparison of the arachidonic acid parameter only. Four replicated chambers were perifused with control medium and each of the experimental arachidonic acid media. This experimental design was repeated using placental tissues from three different patients.

1. Arachidonic Acid Content in Perifused Placental Explants

Placental explants were perifused for five hours with Medium 199 as described above; each was immediately removed from its perifusion chamber, then placed in phosphate buffer (1 ml, 0.05 M, pH 7.6) with 0.1 ml indomethacin (1100 μg/ml DMSO). The tissue was then homogenized and extracted three times with ethyl acetate (3.1 ml). The organic layers were combined and dried under nitrogen. The dried extract was resuspended in chloroform:methanol (20 ml, 2:1) and 1 ml of water. The extract was then divided into a 1 ml aliquot which was spiked with 5 μg arachidonic acid and a 20 ml aliquot which was not spiked. Each aliquot was filtered using a Millipore filter (HVLP 0.45 microns) and the filter rinsed twice with 5 ml of chloroform:methanol (2:1). The extract was emulsified with water (6:1) and centrifuged to separate the aqueous and organic phases. The aqueous phase was discarded and the organic phase dried under nitrogen. A standard arachidonic acid sample (5 μg) was also extracted in a similar fashion. The arachidonic acid in the extract and the spiked extract and the standard sample were quantitated using HPLC (Milton-Roy CM 4000 and spectromonitor 3100). The samples were resuspended in ethanol and chromatographed using a C-18 column (Ultrasphere-ODS, 10×0.5 cm). An isocratic mobile phase of 68% acetonitrile in water was used. Elution was monitored at an optical density at 195 nm and recorded using the Milton-Roy integrator Model C4100. The primary peak of arachidonic acid eluted at approximately 19.9 min and was quantitated by comparison of the height and area under the curve to varying doses of the 5 μg arachidonic acid sample.

Addition of varying doses of arachidonic acid (0.2–10 μg/ml) had no significant effect on PGFM, $TxB_2$ or 6-keto-$PGF_{1\alpha}$, although the endogenous arachidonate was similar to or much less than the doses studied. Only at the 10 μg/ml dose was a delayed increase of PGE and $PGF_{2\alpha}$ observed.

B. RESULTS

Figure 3:
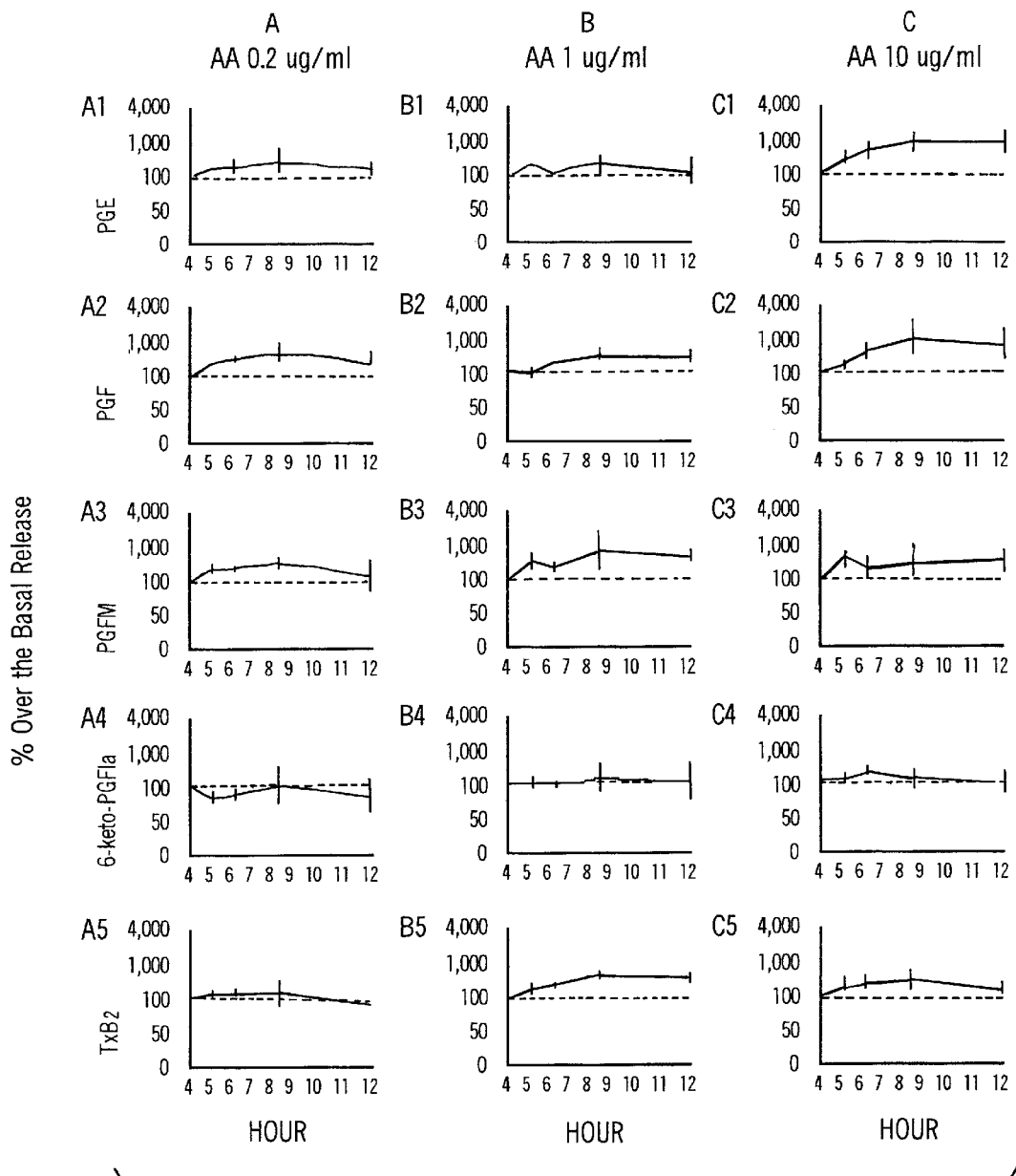
FIG. 3A. Effect of 0.2 µg/ml arachidonic acid on the release of PGE, $PGF_{2\alpha}$, PGFM, 6-keto-$PGF_{1\alpha}$ or $TxB_2$ from human term placenta expressed as percent over control (mean±SEM).
FIG. 3B. Effect of 1 µg/ml arachidonic acid on the release of PGE, $PGF_{2\alpha}$, PGFM, 6-keto-$PGF_{1\alpha}$ or $TxB_2$ from human term placenta expressed as percent over control (mean±SEM).
FIG. 3C. Effect of 10 µg/ml arachidonic acid on the release of PGE, $PGF_{2\alpha}$, PGFM, 6-keto-$PGF_{1\alpha}$ or $TxB_2$ from human term placenta expressed as percent over control (mean±SEM).
Figure 4:
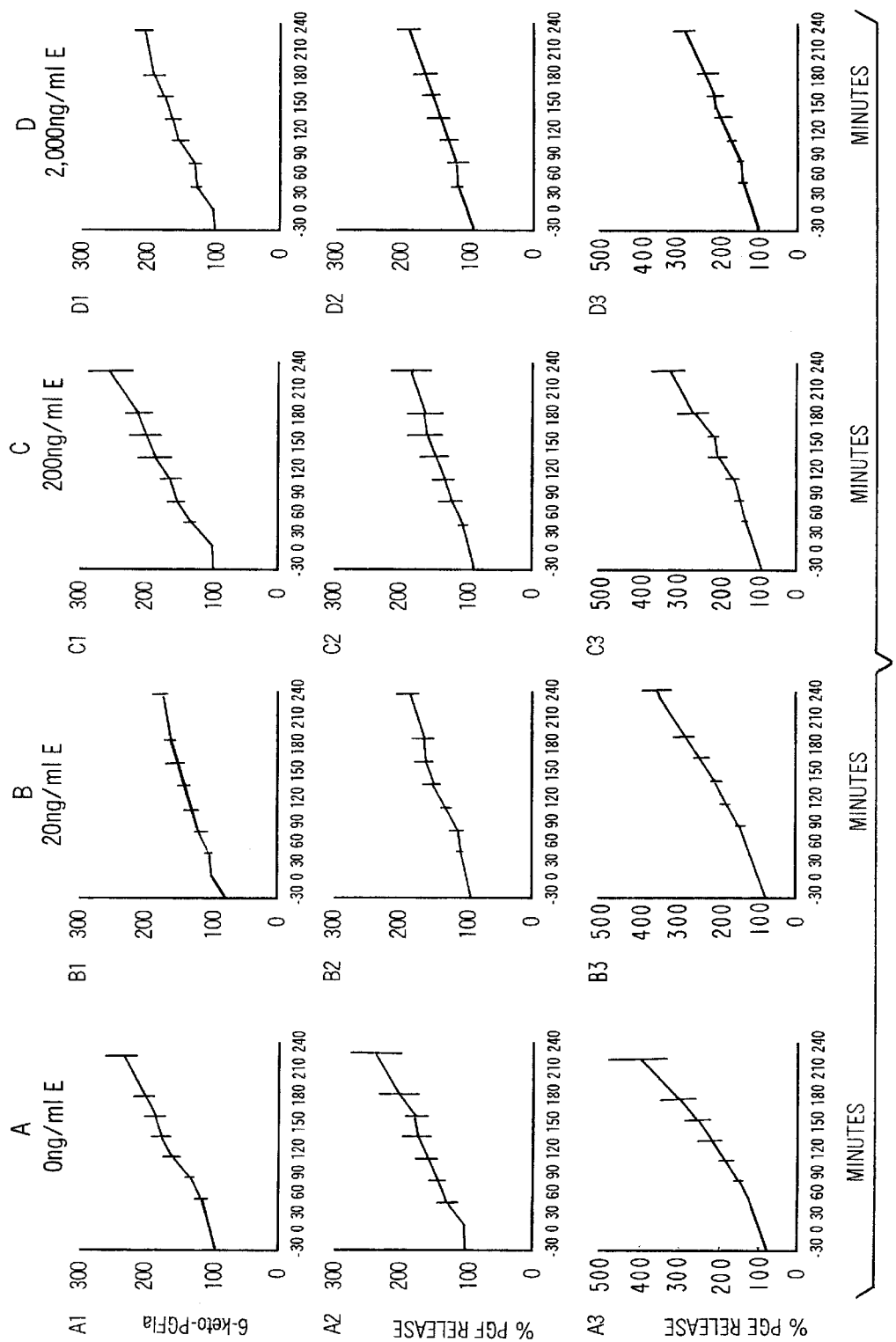
FIG. 4A. The effect of 0 ng/ml estradiol on the fifth-hour normalized release of 6-keto-$PGF_{1\alpha}$, $PGF_{2\alpha}$ and PGE is shown. Points of significant difference are indicated ($^*p<0.02$, $^{**}p<0.05$).
FIG. 4B. The effect of 20 ng/ml estradiol on the fifth-hour normalized release of 6-keto-$PGF_{1\alpha}$, $PGF_{2\alpha}$ and PGE is shown. Points of significant difference are indicated ($^*p<0.02$, $^{**}p<0.05$).
FIG. 4C. The effect of 200 ng/ml estradiol on the fifth-hour normalized release of 6-keto-$PGF_{1\alpha}$, $PGF_{2\alpha}$ and PGE is shown. Points of significant difference are indicated ($^*p<0.02$, $^{**}p<0.05$).
FIG. 4D. The effect of 2,000 ng/ml estradiol on the fifth-hour normalized release of 6-keto-$PGF_{1\alpha}$, $PGF_{2\alpha}$ and PGE is shown. Points of significant difference are indicated ($^*p<0.02$, $^{**}p<0.05$).

1. Prostanoid Recovery and Placental Prostanoid Release in the Presence of Arachidonic Acid FIG. 3A, FIG. 3B and FIG. 3C illustrates the mean percent change over the control release for each hormone at each dose of arachidonic acid studied for the three placentas (%±SEM). Significantly different responses for each prostanoid, comparing the various doses of arachidonic acid over time to controls, using two-way analysis of variance, were noted. Points of significant difference were determined, using the mean normalized response of the three different placentas for each prostanoid studied.

The inclusion of exogenous arachidonic acid in the perifusing medium at 0.2 (FIG. 3A) or 1.0 μg/ml (FIG. 3B) had no significant effect on prostanoid production using this perifusion system. In some instances, increased productions over the control (as indicated by the 100% dashed line) was observed, yet significance was not attained. However, the addition of 10 μg/ml of arachidonic acid did induce a significant increase in PGE and $PGF_{2\alpha}$ release within three hours of exposure of the placental tissue to this precursor (FIG. 3C). Continued perifusion with arachidonic acid resulted in continuation of the significantly increased release of these two prostanoids.

Endogenous free arachidonate in the placental explants after five hours of perifusion, i.e., the time when tissue was first exposed to exogenous arachidonic acid, was found to be $\leq 200$ ng/gram of tissue. Approximately one gram of tissue was used in each chamber. Thus, the doses of exogenous arachidonic acid utilized in these studies were at least 50 fold, 5 fold, or equimolar to the endogenous free arachidonate in the placental explants.

These data demonstrate that prostanoid production from the human term placenta is not limited by arachidonic acid availability, and that enzyme inhibitors of extra-cellular chelating agent have little immediate effect on prostanoid release, with the exception of $PGI_2$. However, increasing arachidonic acid levels to very high concentrations may activate endoperoxide isomerase activity, resulting in increased PGE and $PGF_{2\alpha}$ release. In addition, the production of PGFM appears to be saturated by the endogenous production of $PGF_{2\alpha}$; therefore, the $PGF_{2\alpha}$ produced cannot be totally metabolized by the placenta.

The present findings that increasing the availability of free arachidonic acid to 1 μg/ml did not result in an increase of any of the five prostanoids studied, suggests that availability of arachidonic acid may not be rate-limiting for the term placenta under these conditions. The present demonstration that this concentration of arachidonic acid is at least five times greater than the endogenous tissue arachidonate provides convincing data that substrate availability was not a limiting factor in the production of these placental prostanoids. In addition, it should be appreciated that the hourly production of these five prostanoids would require less than 5% of the endogenous level of free placental arachidonate.

Thus, the present studies support the finding that, in the human placenta, the availability of arachidonate is not the primary rate-limiting step regulating prostanoid production.

In addition, the differing patterns of release among these prostanoids indicate that enzymes beyond the cyclooxygenase are regulating their relative releases. The inventor's finding that the high concentration of 10 $\mu$g/ml of arachidonic acid in the perfusing medium increased only PGE and $PGF_{2\alpha}$ again demonstrates differential regulation of these prostanoids. The observation that this increase of PGE and $PGF_{2\alpha}$ occurred only after two to three hours' incubation with this level of arachidonic acid suggests that induction of increased enzyme activity may have occurred before the increased PGE and $PGF_{2\alpha}$ production could be effected.

EXAMPLE 4

ESTROGEN AND ESTROGEN/PROGESTERONE ON PRODUCTION OF 6-KETO-$PGF_{1\alpha}$, PGE AND $PGF_{2\alpha}$ BY PLACENTA The present example demonstrates that estradiol or a combination of estradiol and placenta, yet does not affect the release of $TxB_2$, PGFM or hCG. The basal release of prostaglandin $E_2$ (PGE), prostaglandin F ($PGF_{2\alpha}$), thromboxane ($TxB_2$) and 6-keto-prostaglandin $F_{1\alpha}$ (6-keto-$PGF_{1\alpha}$) increased from the fifth hour in culture, while the release of 13, 14-dihydro-15-keto-$PGF_{2\alpha}$ (PGFM) remained constant and hCG release decreased. The dose-related effect of estradiol (20–2,000 ng/ml) in the perfusing medium effected no change in the release of $TxB_2$, PGFM or hCG. Only the release of 6-keto-$PGF_{1\alpha}$ was significantly increased at 60–120 min after exposure to 200 ng/ml of estradiol. The cumulative release of 6-keto-$PGF_{1\alpha}$ to estradiol was biphasic with inhibition at the 20 ng/ml dose and stimulation at 200 ng/ml. The concomitant addition of progesterone (2,000 ng/ml) with estradiol (200 ng/ml) significantly inhibited the stimulatory action of estradiol.

The release of PGE and $PGF_{2\alpha}$ was increasingly reduced with increasing does of estradiol, but at no particular time point was the inhibition significant. However, a significant dose-related inhibition of PGE release was found when the cumulative release over the four hours of estradiol exposure was compared to the untreated controls. The addition of progesterone with estradiol (2,000 and 200 ng/ml, respectively) reversed the inhibition of PGE by estradiol alone.

These data demonstrate that physiologic levels of estradiol affect 6-keto-$PGF_{1\alpha}$, PGE and $PGF_{2\alpha}$ release from the human term placenta, but do not significantly alter production of $TxB_2$, PGFM or hCG under these conditions. In these studies, the dose-related action of estradiol on PGE, $PGF_{2\alpha}$, PGFM, $TxB_2$, 6-keto-$PGF_{1\alpha}$ and hCG production is demonstrated, using a perifusion system for human placental explants. In addition, the effect of progesterone in combination with estradiol on the release of these placental prostanoids is provided.

A. MATERIALS AND METHODS
1. Materials

Medium 199 (x2) with Earles' Modified Salts, bicarbonate and L-glutamine without phenol red was purchased from Gibco (Chargin Falls, Ohio). Penicillin, streptomycin, bovine serum albumin estradiol, progesterone and indomethacin were obtained from Sigma Chemicals (St. Louis, Mo).

2. Placental Perifusion

Term placentas were obtained and processed as described in Example 2. Twenty replicate chambers were prepared and each perifused with Medium 199 containing 0.05% BSA, 100 U penicillin and 100 $\mu$g streptomycin per ml at a rate of 6 ml/hour for nine hours. Perifusion was performed for four and one-half hours prior to initiation of sample collection. In this fashion, all tissues were thoroughly washed and equilibrated. Sample collection was every 15 minutes, beginning at four and one-half hours, into 12×75 mm glass tubes containing 0.1 ml indomethacin (1,100 $\mu$g/ml dimethyl sulfoxide [DMSO]). Collection of the effluent of the 20 chambers was done simultaneously, using an ISCO fraction collector Retriever III adapted with a manifold and a rack having 20 tubes.

3. Effect of Estradiol or Estradiol and Progesterone on Placental Prostanoid Release To study the effect of estradiol or estradiol and progesterone on basal prostanoid release, ten minutes prior to the beginning of the fifth hour of the perifusion, Medium 199 in the experimental chambers was changed to Medium 199 containing estradiol (20, 200, 2,000 ng/ml) or to estradiol and progesterone (200 and 2,000 ng/ml, respectively). These concentrations were chosen to simulate concentrations in intrauterine tissues at term. It took ten minutes for the input medium to pass through the perifusion tubing and chamber and to be collected in the sample tube. Four replicated chambers were perifused with each experimental medium, while, in another four replicated chambers, the perifusion was continued with the control Medium 199. This experimental design was repeated using placental tissues from three different patients who had had normal pregnancies.

4. Radioimmunoassays

Radioimmunoassays were performed in a fashion similar to what has been previously described herein at Example 1. Samples collected at −30, 0, 30, 90, 120, 150, 180 and 240 minutes were chosen for assay and for data analyses. All the samples from a given perifusion (placenta) were quantitated in the same assay.

5. Statistical Analysis

Hormonal values for a given chamber were normalized to the fifth hour prostanoid or hCH release for that chamber and expressed as a percent release over the fifth-hour release. Because of differences in the amount of blood vessels and connective tissue among placental explants, the release expressed per unit weight resulted in a higher variance between chambers. On the other hand, expressing each chamber's response in relation to its fifth-hour release resulted in a very low variance between chambers. Thus, the release of each chamber was related to its functional competence at the time of treatment rather than to it mass.

The mean release for replicate chambers from a given placenta for each particular hormone in the presence of each dose of estradiol or estradiol and progesterone at each time point was calculated. Similar calculations were done for the control chambers. The mean data for controls and each treatment for the three different placentas were subject to statistical analyses. Thus, the response for each placenta was weighed equally. For each hormone studied, the normalized data from each placenta were tested for homogeneity using Bartlett's test and, if significant deviation was found, the data were log-transformed prior to statistical analysis. Two-way analysis of variance was used to determine if there was a significant main effect or interaction. If so, one-way analysis of variance and the Student-Newman-Keul test were used to determine the significantly different points as compared to the control. A value of $p<0.05$ was considered to be statistically significant.

In addition, the cumulative release for each hormone from each placenta for each treatment was calculated, using the sum of the normalized release from 30 to 240 minutes. One-way analysis of variance was used to test for statistical effects of treatment. The points of significant variation were determined using the Student-Newman-Keuls test. Linear line regression analysis was used to determine the significance of the dose-response effect of estradiol.

B. RESULTS

The basal release (mean±sem) of $^6$-keto-PGF$_{1\alpha}$, PGF$_{2\alpha}$, PGE, TxB$_2$, PGFM and hCG was 99±37, 562±207, 749±313, 1,680±588, 1,602±639 and 6±2, respectively. When the hormonal release of 6-keto-PGF$_{1\alpha}$, PGF$_{2\alpha}$, PGE, and TxB$_2$ was normalized to the fifth-hour release, each increased from the fifth to the ninth hour in culture to 234%, 228%, 417% and 138%, respectively. However, the release of PGFM was constant during the 4.5 experimental hours of perifusion, whereas the release of hCG declined to 59% of the zero time release during the following hours of perifusion. The release pattern between these three placentas had an average coefficient of variation of only 12.9%, 20.3%, 17.3%, 12.2%, 10.5% and 6.6% for 6-keto-PGF$_{1\alpha}$, PGF$_{2\alpha}$, PGE, TxB$_2$, PGFM and hCG, respectively, over the perifusion period. FIG. 4A, FIG. 4B, FIG. 4C and FIG. 4D illustrates the normalized release patterns (mean±sem) for 6-keto-PGF$_{1\alpha}$, PGF$_{2\alpha}$ and PGE throughout the perifusion period.

Figure 5:
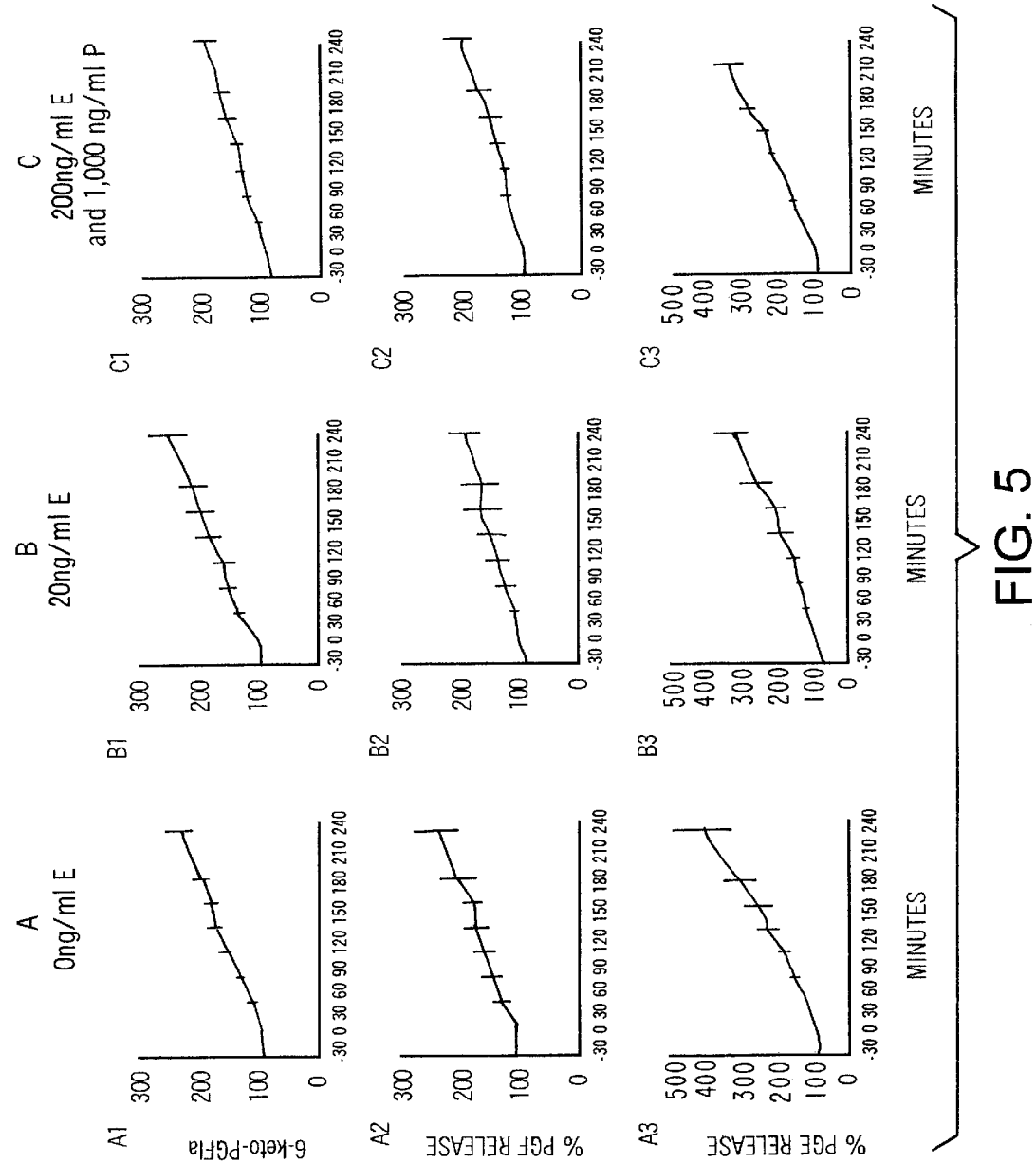
FIG. 5A. The effect of no estradiol or progesterone (control) for the fifth-hour normalized release of 6-keto-$PGF_{1\alpha}$, $PGF_{2\alpha}$ and PGE is shown. Points of significant difference are indicated ($^*p<0.02$, $^{**}p<0.05$).
FIG. 5B. The effect of estradiol alone (200 ng/ml) for the fifth-hour normalized release of 6-keto-$PGF_{1\alpha}$, $PGF_{2\alpha}$ and PGE is shown. Points of significant difference are indicated ($^*p<0.02$, $^{**}p<0.05$).
FIG. 5C. The effect of estradiol and progesterone (200 and 2,000 ng/ml, respectively) for the fifth-hour normalized release of 6-keto-$PGF_{1\alpha}$, $PGF_{2\alpha}$ and PGE is shown. Points of significant difference are indicated ($^*p<0.02$, $^{**}p<0.05$).
Figure 6:
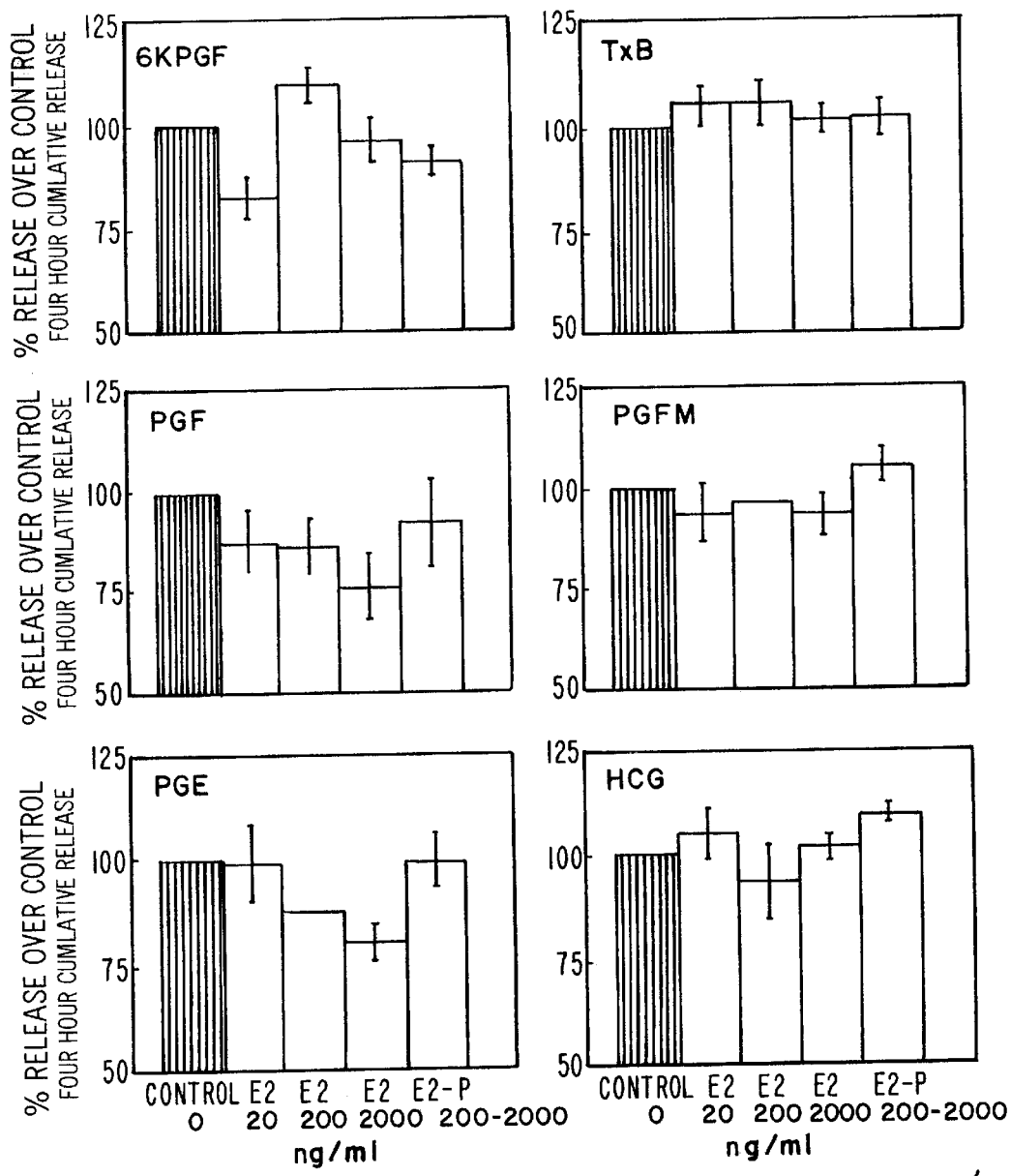
FIG. 6. The cumulative release of 6-keto-$PGF_{1\alpha}$, $PGF_{2\alpha}$, PGE, $TxB_2$, PGFM and hCG, expressed as a percentage of the cumulative release from the controls is illustrated. Points of significant difference are indicated ($^*p<0.02$, $^{**}p<0.05$). Significant dose-related responses are indicated.

The effect of varying doses of estradiol in the perifusion medium on the release of 6-keto-PGF$_{1\alpha}$, PGF$_{2\alpha}$ and PGE is also illustrated in FIG. 4A, FIG. 4B, FIG. 4C and FIG. 4D. A biphasic action of estradiol on the prostacyclin metabolite was observed. Low doses of estradiol resulted in a reduction of 6-keto-PGF$_{1\alpha}$ release, as compared to the physiological dose of estradiol (200 ng/ml) at 60 minutes ($p<0.04$), whereas a physiologic or higher concentration of estradiol led to a stimulation of 6-keto-PGF$_{1\alpha}$ release at 30 minutes ($p<0.02$). Addition of progesterone (2,000 ng/ml) together with the estradiol (200 ng/ml) blocked the stimulatory action of 200 ng/ml estradiol alone (FIG. 5B and FIG. 5C). The cumulative release of 6-keto-PGF$_{1\alpha}$ over the four hours of perifusion was also inhibited by low doses of progesterone ($p<0.02$) and stimulated by physiologic concentration of estradiol (FIG. 6). This cumulative stimulation of 6-keto-PGF$_{1\alpha}$ was reversed by progesterone.

PGF$_{2\alpha}$ release was not significantly affected by the addition of estradiol or estradiol and progesterone to the perifusing medium of these placental explants (FIG. 4B, FIG. 4C, FIG. 4D, FIG. 5B and FIG. 5C), although a trend toward decreasing release with increased estradiol concentration was observed. The cumulative release of PGF$_{2\alpha}$ (FIG. 6) was inhibited in a dose-related fashion with increasing estradiol concentration ($r=0.609$, $p<0.02$).

The release of PGE from these placental explants was also suppressed by the addition of estradiol (FIG. 4A, FIG. 4B, FIG. 4C and FIG. 4D). Although the decrease of PGE release by estradiol was not significant at any given time point, the cumulative release over the four hours of exposure was significantly inhibited ($p<0.05$) (FIG. 6). A dose-related inhibition with increasing estradiol concentration was observed ($r=0.738$, $p<0.005$). The concomitant addition of estradiol and progesterone resulted in a reversal of the estradiol effect (FIGS. 5 and 6).

On the other hand, the release of TxB$_2$, PGFM and hCG was not affected by exposure to estradiol or estradiol and progesterone in the does range studied at any given time point studied. Neither was the cumulative release for TxB$_2$, PGFM nor hCG affected by estradiol or estradiol and progesterone (FIG. 5A, FIG. 5B and FIG. 5C).

In these studies, the action of estradiol or estradiol and progesterone at concentrations lower than, similar to, or higher than intrauterine concentrations in normal term placentas was defined. Estradiol was demonstrated to modulate placental 6-keto-PGF$_{1\alpha}$ production in a biphasic fashion, whereas it inhibits PGE and PGF$_{2\alpha}$ release in a dose-related fashion. Yet, in the presence of physiological concentration of progesterone, the action of estradiol by itself can be reversed.

In the studies reported herein, no significant changes were observed for PGFM with estradiol alone or in combination with progesterone. The action of progesterone alone was not examined. In prior studies by the present inventor, changes in PGFM release from human term placental explants were not affected, which led to the finding that the enzymatic capacity of the metabolizing enzyme(s) was saturated.

6-Keto-PGF$_{1\alpha}$, the metabolite of prostacyclin, is a potent vasodilator, and is thought to play an important role in vasodilation of the placenta. Thus, a stimulation of 6-keto-PGF$_{1\alpha}$ release is contemplated by the present methods to lead to vasodilation, or an inhibition in its production may lead to vasoconstriction. Estradiol at low levels has an inhibitory action on 6-keto-PGF$_{1\alpha}$, whereas physiologic levels stimulate placental 6-keto-PGF$_{1\alpha}$ release. Although other investigators have also observed the stimulatory role of estradiol on 6-keto-PGF$_{1\alpha}$ release, no inhibitory action has been noted. This difference might be related to different culture systems. The present studies were done using explants in serum-free defined media, whereas previous studies utilized a cell culture system in a medium containing 10% horse serum. The stimulatory action of physiological concentrations of estradiol can be overridden by progesterone and may lead to decreased prostacyclin production. Increased placental progesterone production in preeclampsia in the presence of normal estradiol levels has been proposed as a causative factor of the reduced prostacyclin production characteristic of this disease.

Thromboxane B$_2$ (TxB$_2$) concentrations were not affected by estradiol or estradiol and progesterone in the medium. Human chorionic gonadotropin (hCG) release from explants fell dramatically during the study period. Addition of estradiol resulted in small prostanoid changes, but did not alter the spontaneous decline of hCG.

Two other factors that have been shown to affect both prostanoid production and steroid release in the human placenta are GnRH and IGF-I. GnRH is shown in the present studies to inhibit PGE, PGF$_{2\alpha}$ and TxB$_2$. This response may be due to the increased progesterone and estrogen production that results from GnRH-stimulated hCG release. The inhibition of PGE and PGF$_{2\alpha}$ observed herein could be consistent with a steroid-mediated mechanism for GnRH action, but no decrease in TxB$_2$ was found. This GnRH action would have to have been effected through a different mechanism.

IGF-I, which inhibits estrogen and stimulates progesterone, is demonstrated to effect an inhibition of PGF$_{2\alpha}$ and TxB$_2$. However, these studies on the effect of low estradiol, alone or in combination with progesterone, did not result in a similar pattern of inhibited prostanoid release (see Example 6). Thus, factors other than steroids should also be involved in the IGF-I action on placental prostanoid production.

EXAMPLE 5

DEXAMETHASONE EFFECT ON PLACENTAL PROSTANOID PRODUCTION

In the present example, fresh placental tissue in a placental explant perifusion system is used to demonstrate the effect of dexamethasone on PGE, $PGF_{2\alpha}$, PGFM, $TxB_2$ and 6-keto-$PGF_{1\alpha}$ production. In addition, the effect of GnRH in combination with dexamethasone on human term placental prostanoid release is demonstrated.

A. MATERIALS AND METHODS

1. Effect of Dexamethasone and GnRH on Placental Prostanoid Release

The perifusion system described at Examples 2 and 3 was used in the present study. At the end of the fourth hour of the perifusion, Medium 199 in th experimental chambers was changed to Medium 199 containing dexamethasone ($10^{-6}$ M), or to GnRH ($10^{-17}$ M), or to dexamethasone and GNRH ($10^{-8}$ M and $10^{-7}$ M, respectively). It took one hour for the input medium to pass through the perifusion tubing and chamber and to be collected in the sample tube. Four replicated chambers were perifused with each of the three experimental media, while, in another four replicated chambers, the perifusion was continued with the control Medium 199. This experimental design was repeated using placental tissues from three different patients, each of whom had a normal pregnancy.

2. Statistical Analysis

Hormonal values for a given chamber were normalized to the fifth-hour prostanoid release for that chamber, expressed as a percent release over the fifth-hour release. The mean release for replicate chambers from a given placenta for each particular hormone in the presence of GnRH, dexamethasone, or GnRH and dexamethasone at each point was calculated. Similar calculations were done for the control chambers. The mean data for each treatment for the three different placentas were subjected to statistical analyses. Thus, the response for each placenta was weighed equally. Two-way analysis of variance was used to determine if there was significant main effect or interaction. If so, one-way analysis of variance and Student-Newman-Keuls test were used to determine the significantly different points as compared to the control ($p<0.05$ was considered to be statistically significant).

In addition, the cumulative release for each hormone from each placenta for each treatment was calculated. One-way analysis of variance was used to test for statistically significant effects of treatment. The points of significant variation were determined using Student-Newman-Keuls' test.

B. RESULTS

Figure 7:
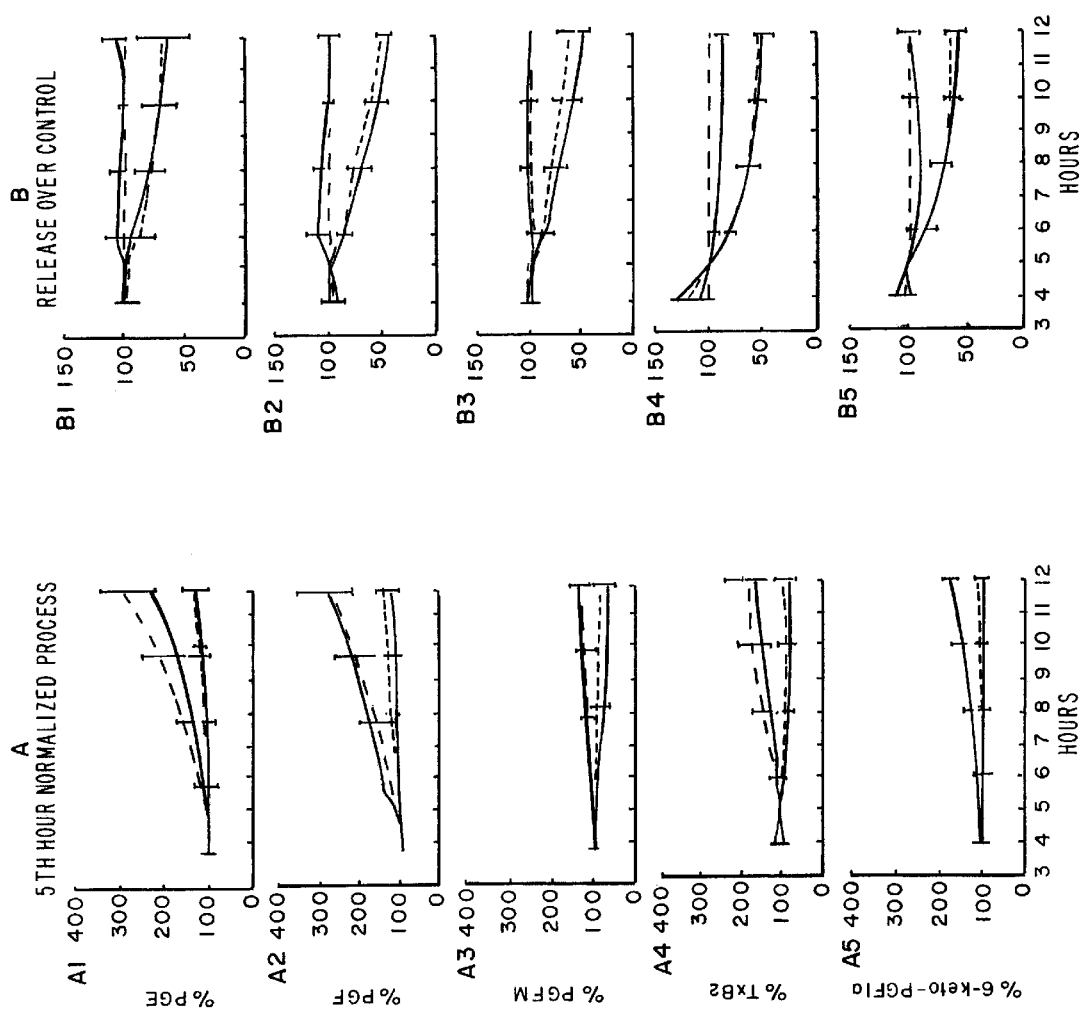
FIG. 7A. The release of PGE, $PGF_{2\alpha}$, PGFM, $TxB_2$ and 6-keto-$PGF_{1\alpha}$ (mean±SEM) from human placental explants, normalized to the fifth-hour release for controls, —●—; GnRH ($10^{-7}$ M),—■—; dexamethasone ($10^{-8}$ M), —O—; GnRH and dexamethasone ($10^{-7}$ M and $10^{-8}$ M), —□—$^*P<0.05$.
FIG. 7B. The release of PGE, $PGF_{2\alpha}$, PGFM, $TxB_2$ and 6-keto-$PGF_{1\alpha}$ (mean±SEM) from human placental explants, as normalized to the control release at each time point is shown, —●—; GnRH ($10^{-7}$ M),——; dexamethasone ($10^{-8}$ M), —O—; GNRH and dexamethasone ($10^{-7}$ M and $10^{-8}$ M), —□—$^*P<0.05$.

The basal release of PGE, $PGF_{2\alpha}$, PGFM, $TxB_2$ and 6-keto-$PGF_{1\alpha}$ normalized to the fifth-hour release, increased to 294%, 275%, 190%, 176% and 140%, respectively, by the twelfth hour in culture. The release pattern between these three placentas had an average coefficient of variation of only 19%, 18%, 16%, 27%, and 6% for $PGF_{2\alpha}$, PGE, PGFM, $TxB_2$ and 6-keto-$PGF_{1\alpha}$, respectively, over the perifusion period. FIG. 7A illustrates the fifth-hour normalized release pattern (mean±sem) for each of these prostanoids throughout the perifusion period.

Addition of GNRH effected, within the first hour of exposure to GnRH ($10^{-7}$ M), an inhibition of $TxB_2$ that continued throughout the perifusion period (FIGS. 7A and 7B). This finding was expected from the inventor's prior studies using this concentration of GNRH. Dexamethasone ($10^{-8}$ M) effected a marked inhibition of each of the prostanoids—PGE, $PGF_{2\alpha}$, PGFM, $TxB_2$ and 6-keto-$PGF_{1\alpha}$. For PGE, $PGF_{2\alpha}$, PGFM, $TxB_2$ and 6-keto-$PGF_{1\alpha}$, the inhibition was already significant within the first hour of incubation with dexamethasone. Only the inhibition of PGFM lagged by one hour. By the seventh hour of incubation with dexamethasone, the suppression of PGE was 68% of its control release, whereas that for $PGF_{2\alpha}$ was 52%; for PGFM, 65%, for $TxB_2$, 53%; and for 6-keto-$PGF_{1\alpha}$, 63%). FIG. 7B illustrates the inhibition of release (mean±SEM) for each of these prostanoids as compared to the mean control release at the same time point, and better depicts the marked inhibition of prostanoid release effected by dexamethasone.

Addition of GnRH ($10^{-7}$ M) together with dexamethasone ($10^{-8}$ M) did not alter the action of dexamethasone alone in the case of PGE, $PGF_{2\alpha}$, PGFM, $TxB_2$ and 6-keto-$PGF_{1\alpha}$ release. However, PGFM release was significantly inhibited in the presence of both GnRH and dexamethasone by the first hour and, after seven hours of perifusion, was reduced to 50% of its zero time release.

Figure 8:
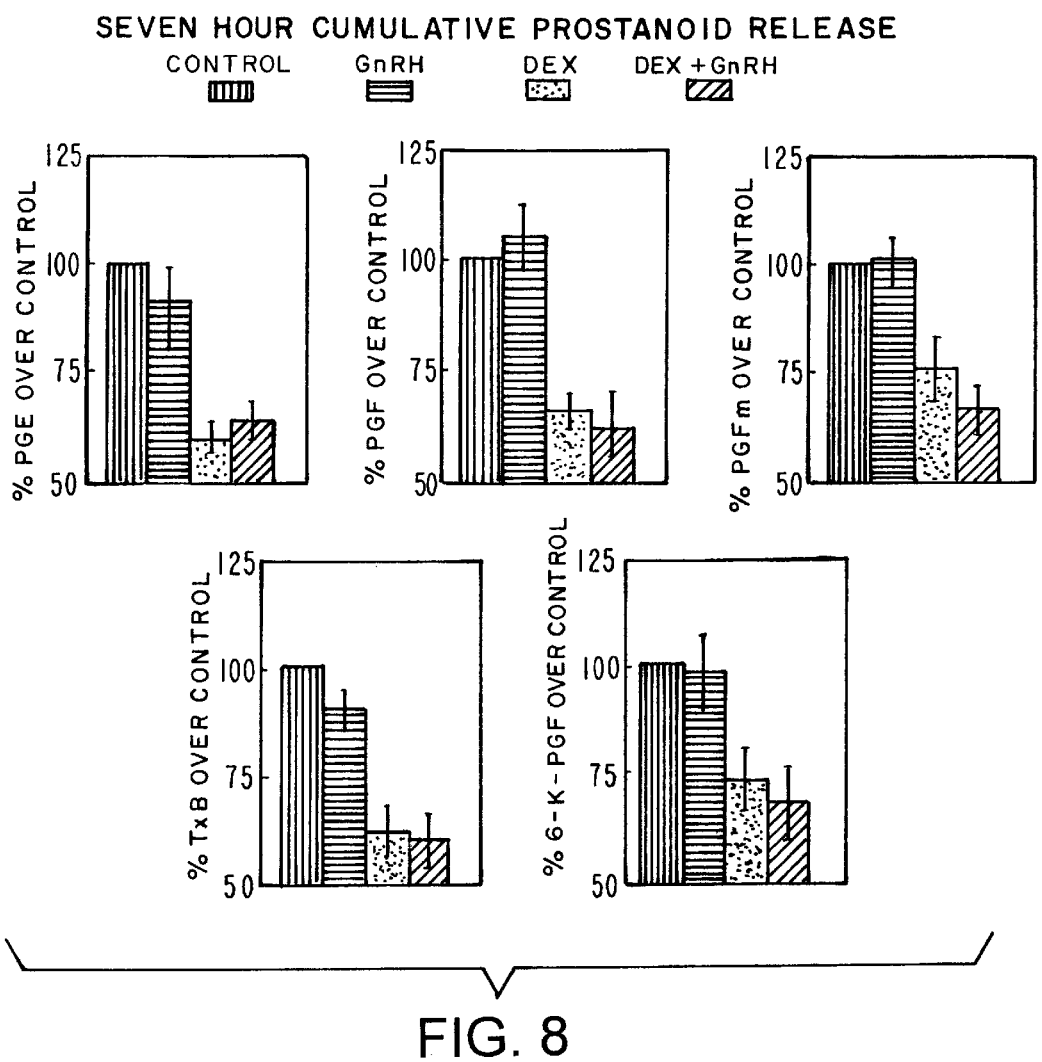
FIG. 8. The cumulative release of PGE, $PGF_{2\alpha}$, PGFM, $TxB_2$ and 6-keto-$PGF_{1\alpha}$ (mean±SEM) from human placental explant with or without exposure to GnRH ($10^{-7}$ M), dexamethasone ($10^{-8}$ M) or GnRH and dexamethasone ($10^{-7}$ M and $10^{-8}$ M) as compared to the control is shown $^{}p<0.01$, $^{*}p<0.001$. Symbols: control, filled; GnRH, horizontal lines; dexamethasone, open; GnRH and dexamethasone, diagonal lines.

The cumulative release (mean±SEM) for each of these prostanoids over the seven hours of perifusion for each treatment is shown in FIG. 8. The cumulative release of PGE was significantly inhibited to 66%±4% by dexamethasone or 69%±3% by dexamethasone and GnRH ($p<0.0003$), whereas $PGF_{2\alpha}$ was suppressed to 71%±4% or 73%±8%, respectively, by these two treatments ($p<0.0008$) and further inhibited by the combination of dexamethasone and GNRH to 67%±5%. Although the cumulative PGFM release was less for GnRH and dexamethasone combined, as compared to dexamethasone alone, there was not a statistically significant difference. $TxB_2$ was inhibited by dexamethasone to 62%±6% of the controls and by the combination of dexamethasone and GnRH to 50%±5% ($p>0.0009$). The inhibition of 6-keto-$PGF_{1\alpha}$ was similar for dexamethasone and dexamethasone and GnRH—73%±7% and 68%±3%, respectively ($p<0.0075$).

Both PGE and $PGF_{2\alpha}$ were produced in approximate equimolar ratios, about one half to one third that of $TxB_2$, whereas 6-keto-$PGF_{1\alpha}$ was produced in relatively lesser amounts than the other prostanoids. The release of PGFM at the fifth hour of perifusion was greater (1.5 times) than that of the prostaglandins, yet it did not increase during the perifusion period. However, the basal release for PGE, $PGF_{2\alpha}$, PGFM, $TxB_2$ and 6-keto-$PGF_{1\alpha}$ increased during the fifth to the twelfth hour of perifusion. From these data and previous findings Kang et al. (1991) Am. J. Obstet. Gynecol., 165:1771–1776), at least one of the enzymes that metabolizes $PGF_{2\alpha}$ appears to be saturated under these incubation conditions.

In these studies, dexamethasone ($10^{-8}$ M) is demonstrated to be a potent inhibitor of prostanoid release from the human term placenta. Previous studies have described the effect of glucocorticoids on prostaglandin release from the placenta; however, their effect on PGFM, $TxB_2$ or 6-keto-$PGF_{1\alpha}$ was not reported.

From these data, a role for ACTH and/or glucocorticoids in the modulation of placental cyclooxygenase activity may be proposed, because all the prostanoids were inhibited. In addition, the basal increase in prostanoids observed in human term explant cultures may reflect increasing CRH/ACTH or decreasing cortisol inhibition in these term tissues. The finding that dexamethasone suppresses the prostanoids suggests the latter possibility, i.e., that decreasing cortisol inhibition of ACTH may be the operative mechanism in these placental cultures. High dexamethasone may inhibit ACTH release in these tissues, and thus decrease prostanoid production. Other mechanisms to effect the maintenance of basal prostanoid production may also be operative, such as the dexamethasone suppression of lipacortins, which leads to a suppression of prostaglandins.

The observation that GnRH had no further action on prostanoid release indicates that the magnitude of the dexamethasone suppression was so great that the small effect of GnRH could not be appreciated. The hastening of the PGFM inhibition in the presence of GnRH combined with dexamethasone may indicate that this dose of GnRH may also act on the early inhibition of $PGF_{2\alpha}$ metabolism. The present study clearly indicates that glucocorticoids can be potent regulators of human term placental prostanoid release and that their role in physiological homeostasis of placental paracrine function may be highly significant in the appropriate maintenance of pregnancy, the initiation of labor and normal fetal outcome.

EXAMPLE 6

IGF-I INHIBITION OF THROMBOXANE AND PROSTAGLANDIN $F_{2\alpha}$ PRODUCTION BY PLACENTA The present example demonstrates the selective inhibition of thromboxane $B_2$ and $PGF_{2\alpha}$ provided by insulin-like growth factor treatment of human placental cells. This example also demonstrates the utility of the claimed methods for regulating labor in an animal, such as in farm animals and humans. Using the findings of the present example, insulin-like growth factor and specific inhibitors of insulin-like growth factor, may be used to inhibit a pre-term onset of labor (administer IGF-I), or to induce labor in a gestational post-term pregnancy (administer an inhibitor of IGF-I or reduce concentrations or activity of IGF-I in vivo).

A. MATERIALS AND METHODS
1. Placental Perifusion

Term placentas were obtained and processed as described herein. Seven replicate chambers were prepared and each perifused with Medium 199 containing 0.05% BSA, penicillin (100 U/ml), streptomycin (100 µg/ml), estradiol (200 ng/ml), progesterone (2000 ng/ml), dexamethasone ($10^{-8}$ M), and insulin (100 µU/ml), at a rate of 6 ml/hour for 10.5 hours. Steroids were first dissolved in ethanol at $10^{-4}$M final concentration and taken to final dilution with BSA-containing medium. This medium is hereafter in this Example, referred to as Medium 199. These concentrations of steroid were chosen because they are known by those in the obstetrical arts to simulate the intrauterine milieu in vivo in humans. The influx medium was aerated with 95% air and 5% $CO_2$ throughout the perifusion. Perifusion at a rate of 6 ml/hr was performed for four hours prior to initiation of sample collection. In this fashion, all tissues were thoroughly washed and equilibrated. Samples were collected every half-hour, beginning at the start of the fourth hour, into 12×75 mm glass tubes containing 0.1 ml indomethacin (1100 µg/ml dimethyl sulfoxide [DMSO]). Collection of the effluent of the seven chambers was done simultaneously, using an ISCO fraction collector Retriever III adapted with a rack having seven tubes and a manifold.

To study the effect of IGF-I on basal prostanoid release, ten minutes prior to the beginning of the fifth hour of the perifusion, Medium 199 in the experimental chambers was changed to Medium 199 containing IGF-I ($10^{-8}$ M). This dose of IGF-I was chosen from calculations of the inventor using the Km of the placental receptor for IGF-I. It took ten minutes for the input medium to pass through the perifusion tubing and chamber and to be collected in the sample tube. Three replicated chambers were perifused with experimental medium, whereas, in another four replicated chambers, the perifusion was continued with the control, Medium 199. This experimental design was repeated using placental tissues from three different patients each having a normal pregnancy.

2. Prostanoid Recovery and Stability; Prostanoid Radioimmunoassays

Prostanoid recovery and stability was determined as described in Example 1. Prostanoid radioimmunoassay and all other materials and methods were also conducted as described in Example 1.

3. Statistical Analysis

Hormonal values for a given chamber were normalized to the fifth-hour prostanoid or hCG release for that chamber, expressed as a percent release over the fifth-hour release. The mean release for replicate chambers from a given placenta for each particular hormone in the presence of IGF-I at each time point was calculated and the mean data for each of the three different placentas were averaged at each time point. Thus, each placenta was weighed equally in the statistical analyses. Similar calculations were done for the controls as for the experimental chambers. For each hormone studied, these average normalized data were tested for homogeneity, using Bartlett's test, and if significant deviation was found, the data were log-transformed prior to statistical analysis. Two-way analysis of variance was used to determine if there was significant main effect or interaction. If so, one-way analysis of variance and Student-Newman-Keuls test were used to determine the significantly different points as compared to the control ($P<0.05$ was considered to be statistically significant).

In addition, the cumulative release for each hormone from each placenta for each treatment was calculated. One-way analysis of variance was used to test for statistical effects of treatment. The points of significant variation were determined using the Student-Newman-Keuls test.

B. RESULTS

The basal release of prostaglandin $E_2$ (PGE), prostaglandin F ($PGF_{2\alpha}$), thromboxane ($TxB_2$) and 6-keto-prostaglandin $F_{1\alpha}$(6-keto-$PGF_{1\alpha}$) increased from the fifth hour in culture, while the release of 13, 14-dihydro-15-keto-$PGF_{2\alpha}$ (PGFM) remained constant and hCG release decreased in control cultures. The addition of IGF-I($10^8$ M) to the perifusing medium effected a significant inhibition of $PGF_{2\alpha}$ within two and one-half hours of exposure. However, the release of PGE was not altered.

The basal release (mean±SEM) of $TxB_2$, 6-keto-$PGF_{1\alpha}$, $PGF_{2\alpha}$ and PGE, when normalized to the fifth-hour release, increased from the fifth to the tenth hour in culture 136%, 164%, 145% and 228%, respectively. However, the release of PGFM did not vary significantly during these hours of perifusion, whereas the release of hCG declined to 52% of the fifth-hour release during the following five hours. The release pattern between different placentas had an average coefficient of variation of only 6.5%, 11.6%, 9.5%, 12.2%, 18.0% and 8.9% for $TxB_2$, 6-keto-$PGF_{1\alpha}$, $PGF_{2\alpha}$, PGE, PGFM AND hCG, respectively, over the perifusion period. The solid lines in FIG. 9A, FIG. 9B, FIG. 9C, FIG. 9D, FIG. 9E and FIG. 9F illustrate the normalized release patterns (mean±SEM) for these prostanoids throughout the perifusion period.

Figure 9:
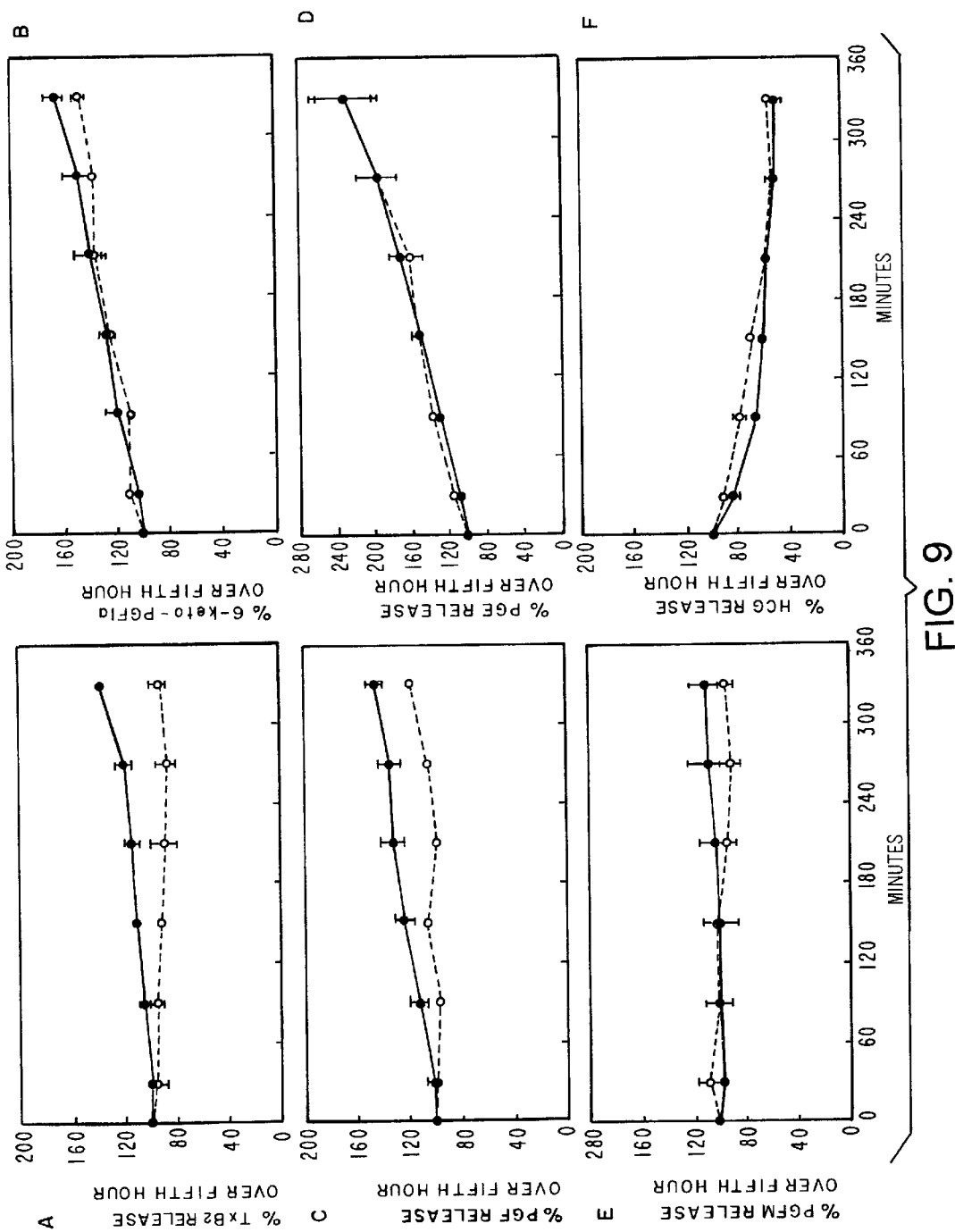
FIG. 9A. The release (mean±SEM) of $TxB_2$ from replicate cultures of three different human term placentas throughout the 330 minutes of IGF-I treatment (■—■) or for controls (●—●) is shown. Significant difference are noted $^*P<0.05$, $^{**}P<0.01$ FIG. 9B. The release (mean±SEM) of 6-keto-$PGF_{1\alpha}$ from replicate cultures of three different human term placentas throughout the 330 minutes of IGF-I treatment (■—■) or for controls (●—●) is shown. Significant difference are noted $^*P<0.05$, $^{**}P<0.01$.
FIG. 9C. The release (mean±SEM) of $PGF_{2\alpha}$ from replicate cultures of three different human term placentas throughout the 330 minutes of IGF-I treatment (■—■) or for controls (●—●) is shown. Significant difference are noted $^*P<0.05$, $^{**}P<0.01$.
FIG. 9D. The release (mean±SEM) of PGE from replicate cultures of three different human term placentas throughout the 330 minutes of IGF-I treatment (■—■) or for controls (●—●) is shown. Significant difference are noted $^*P<0.05$, $^{**}P<0.01$.
FIG. 9E. The release (mean±SEM) of PGFM from replicate cultures of three different human term placentas throughout the 330 minutes of IGF-I treatment (■—■) or for controls (●—●) is shown. Significant difference are noted $^*P<0.05$, $^{**}P<0.01$.
FIG. 9F. The release (mean±SEM) of hCG from replicate cultures of three different human term placentas throughout the 330 minutes of IGF-I treatment (■—■) or for controls (●—●) is shown. Significant difference are noted $^*P<0.05$, $^{**}P<0.01$.

The addition of IGF-I ($10^8$ M) to the perifusing medium resulted in a highly significant ($P<0.003$) reduction of $TxB_2$ release (FIG. 9A). Normally, its release would increase about 1.6 times over control during the treatment period. However, exposure to IGF-I resulted in a significant inhibition of $TxB_2$ release by 150 minutes following treatment, decreasing to 85% of the control's release by the fifth hour of treatment.

The release of the prostacyclin metabolite, 6-keto-$PGF_{1\alpha}$, was not significantly altered by exposure for more than five hours to IGF-I (FIG. 9B). Its release continued to increase during the five hours, attaining 146% of the fifth-hour release.

However, the release of $PGF_{2\alpha}$ was significantly (P<0.01) inhibited by IGF-I (FIG. 9C). This inhibition of $PGF_{2\alpha}$ release was significant beginning from the third hour perifusion. By the fifth hour of treatment with IGF-I, the $PGF_2a$ release was 116%, which was not significantly different from the control's release. On the other hand, PGE, which also increased during the test period, was not affected by IGF-I (FIG. 9D). In the IGF-I treated tissues, the PGE increased to 228% of the fifth-hour release, as did the control tissues.

PGFM release was unchanged during the five hours of perifusion by the addition of IGF-I to the medium (FIG. 9E). As for the controls, PGFM did not increase throughout the perifusion.

The addition of IGF-I to the medium did not affect the release of the hCG as compared to the controls (FIG. 9F). HCG declined in the presence of IGF-I to 55% of the fifth-hour release, which was not significantly different from the control's release.

Figure 10:
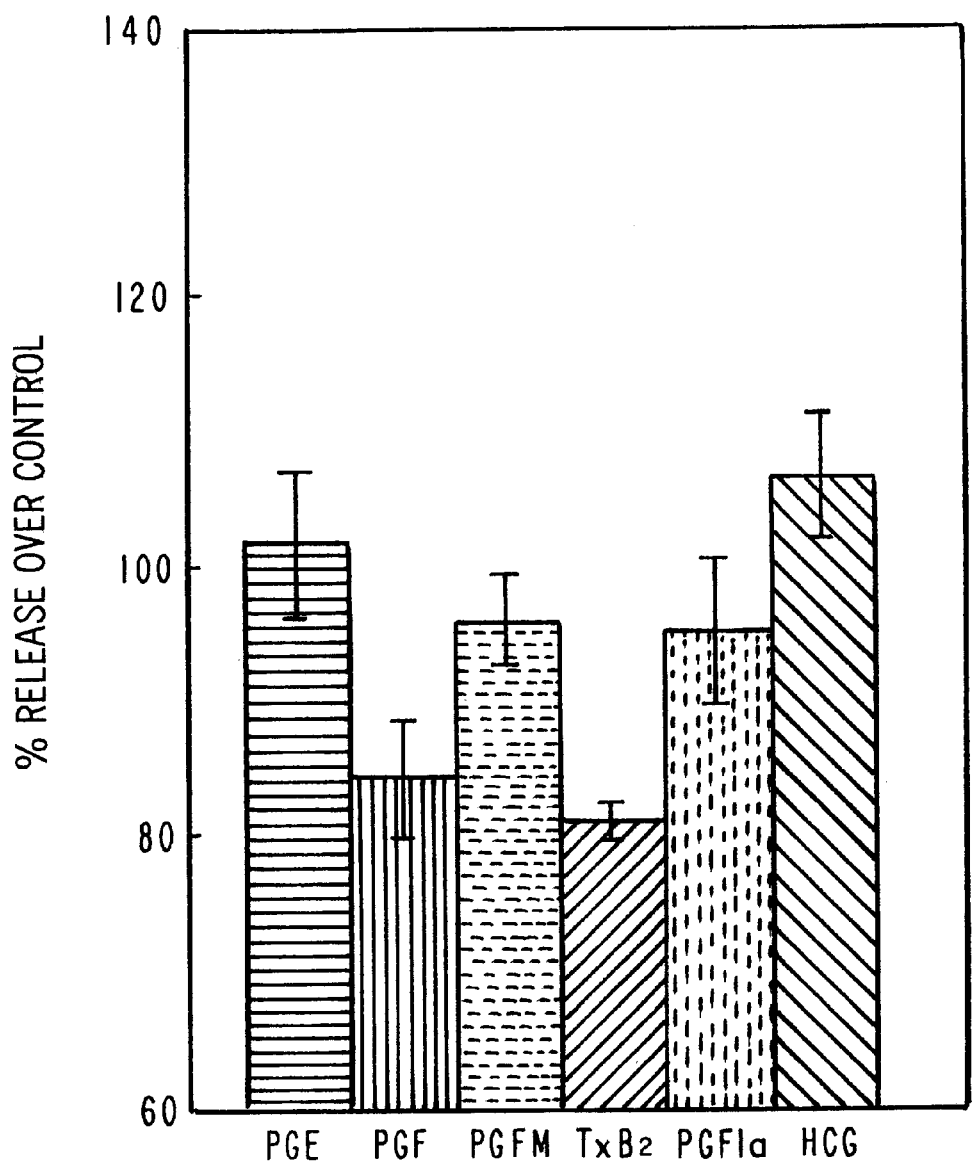
FIG. 10. The cumulative release for PGE, $PGF_{2\alpha}$, PGFM, $TxB_2$, 6-keto-$PGF_{1\alpha}$ and hCG for the IGF-I treatments from replicate explants of three different human term placentas as a percent of the controls' release is shown. Significant difference are noted, $^*P<0.05$, $^{**}P<0.01$.
Figure 11:
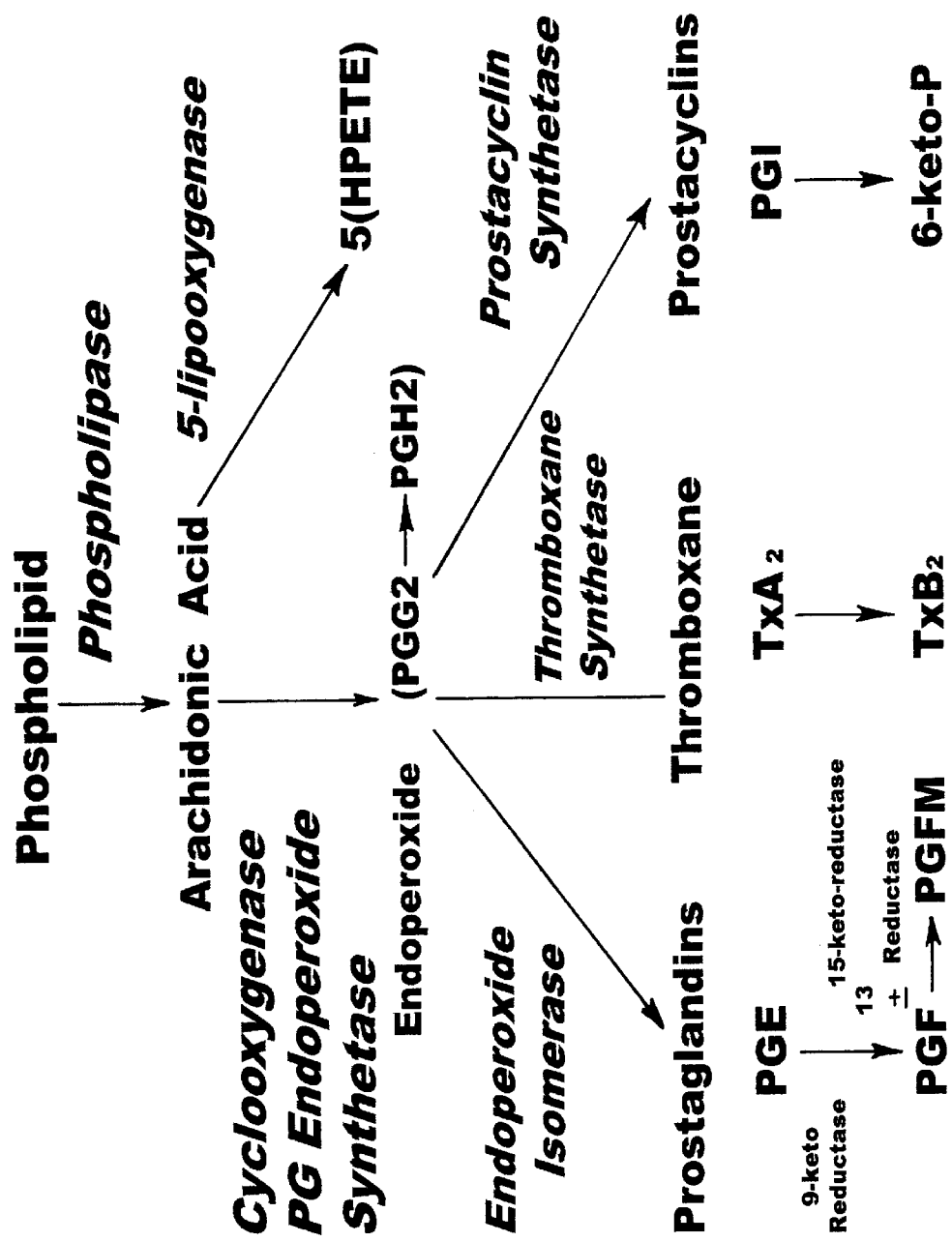
FIG. 11. Biosynthetic pathway of phospholipids to prostaglandins, thromboxane, and prostacyclins.

The cumulative release for each prostanoid and hCG in the presence of IGF-I is shown in FIG. 10. For each hormone, the cumulative release from the treated tissues was compared to cumulative release from the control tissues and expressed as the percent of the control. A significant reduction in $PGF_{2\alpha}$ and $TxB_2$ releases (P<0.05 and 0.01, respectively) was observed with no significant change for the other hormones studied. Because both $TxB_2$ and $PGF_{2\alpha}$ are vaso-constrictors, IGF-I may also act to enhance vasodilation in the placenta as well as to manage uterine contractility during labor.

EXAMPLE 7

DOSE-RELATED ACTION OF Insulin-like GROWTH FACTOR ON BASAL THROMBOXANE PRODUCTION FROM HUMAN TERM PLACENTA The present example demonstrates that the inhibition of thromboxane $B_2$ production from placental cells by IGF-I is dose dependent. Dose related effects of IGF-I on human placental production of PGE, $PGF_{2\alpha}$, PGFM, and 6-keto-$PGF_{1\alpha}$ is also demonstrated.

The dose-related effect of IGF-I on placental prostanoids was studied with the perifusion system previously described herein. Normal term deliveries were perifused with a defmed Medium 199 containing no phenol red nor exogenous hormonal factors other than 100 $\mu$U/ml of insulin, estradiol (200 ng/ml), progesterone (4000 ng/ml) and dexamethasone ($10^-$8). These doses were chosen to emulate the normal term placental environment. Replicate chambers for the control (n=4) and treatment (n=3) explants for each placenta were made. Following a five-hour perifusion at 6 ml/hr with basal media, IGF-I (5, 10, 20, 40 or 80 ng/ml) was added to the triplicate chambers and sample collection continued every 30 minutes for another five hours. The average hormonal response for the replicate chambers of the control and the IGF-I treated explants was calculated and then the mean (±SEM) response for the different placentas with and without treatment was computed and the results compared. $TxB_2$ and $PGF_{2\alpha}$ production were greatly reduced by IGF-I, whereas only a small reduction in PGE at a high dose of IGF-I was observed. $TxB_2$ was inhibited at even 10 ng/ml of IGF-I.

The basal release of thromboxane $B_2$ was relatively constant throughout the test period (i.e., 5th–10th hr. of placental perifusion). The addition of IGF-I at each dose indicated above resulted in the statistically significant inhibition of $TxB_2$ production. The magnitude of the inhibition was directly related to the dose of IGF-I, with $10^{-8}$M affecting the greatest inhibition—a 70% of the basal release.

These data demonstrate that IGF-I specifically inhibits vasoconstrictive prostanoid production by human placental explants in a dose-related manner, and that the active doses are well within a physiological range. Therefore, appropriate doses of IGF-I may be determined for human use in the inhibition of labor using standard pharmacological parameters known to those of skill in the art to provide the described inhibition of thromboxane and prostaglandin $F_{2\alpha}$ by placenta in vivo.

EXAMPLE 8

USE OF IGF-I TO MEASURE PLACENTAL THROMBOXANE INHIBITION IN A BIOLOGICAL FLUID SCREENING ASSAY

The present invention may be employed in methods to measure thromboxane $B_2$ activity in a biological sample. The level of $TxB_2$ in biological fluids, i.e., blood, amniotic fluid, may also be used to evaluate the hormonal function of pregnancy and predict its outcome. Such information may indicate therapeutic treatment to effect normal levels and this appropriate regulate hormonal levels, leading to a better outcome of the pregnancy.

One of the demonstrated utilities of the inventive methods is to measure IGF-I induced inhibition of prostaglandin $F_{2\alpha}$ production by human placental cells, as demonstrated in the study of Example 6.

PROPHETIC EXAMPLE 9

PROPOSED PRODUCTION OF ANTIBODIES SPECIFIC FOR HUMAN Insulin-like GROWTH FACTOR The present example is provided to outline a method whereby antibodies having specific binding affinity for human IGF-I may be prepared for use as a specific inhibitor of IGF-I. The inhibitor of IGF-I may then be used as a pharmacological agent to reduce IGF-I levels in vivo, and eliminate Thromboxane inhibition and $PgF_{2\alpha}$ inhibition in a pregnant animal.

Balb/c mice may be immunized by intraperitoneal administration (ea. 100 mg each) of IGF-I by a standard dosage schedule sufficient to promote the production of anti-IGF-I antibodies in the animal. Mouse spleen cells from animals immunized with the IGF-I antigen may then be fused with P3K myeloma cells, or any immortal cancer cell, to form hybrid cells (hybridomas). The hybrid cells may then be plated and grown in HAT media.

Monoclonal antibody secreted in the media of cultures of the hybrid cells may then be collected. The monoclonal antibodies specific for IGF-I may then be employed as an inhibitor of IGF-I, thereby reducing IGF-I concentrations and reducing the potential of IGF-I mediated inhibition of thromboxane production and prostaglandin $F_{2\alpha}$ by human placental cells. These antibodies may also be formulated so as to be suitable for human use, and employed in the herein disclosed methods to induce labor, or at least to prevent the inhibition of labor, in a pregnant patient.

PROPHETIC EXAMPLE 10

PROPOSED USE OF Insulin-like GROWTH FACTOR-I TO AFFECT A STATE OF PREGNANCY Insulin-like growth factor-1 is a polypeptide hormone present in the intra-uterine tissue during pregnancy. IGF-I is shown in the present studies to be useful in regulating the production of intra-uterine prostanoids. The prostanoids thromboxane and prostaglandin F are both vasoconstrictors, and play a significant role in the regulation of intra-uterine blood flow and uterine contractility during pregnancy.

Vasoregulation in Pregnancy

As illustrated in FIG. 9A, FIG. 9B, FIG. 9C, FIG. 9D, FIG. 9E, FIG. 9F and 10, IGF-I is effective in inhibiting thromboxane and prostaglandin F production by the placenta. Thus, by regulating the concentrations of intra-uterine IGF-I levels, either by altering its production, its metabolism or its activity, the production of thromboxane and prostaglandin F can be altered, leading either to increased or decreased vasoconstriction. Thus, increasing IGF-I may be used in inhibiting vasoconstriction. Therefore, IGF-I treatment could be used to inhibit intra-uterine vascular diseases in pregnancy through its affect on vasoconstrictive prostanoids (see Example 11).

The present methods may also be used in treating pregnancy induced hypertension, to reduce placental resistance, and to increase blood flow and thus nutrient flow to the fetus. The activity of IGF-I in placental prostanoid production is a novel finding which may be therapeutically implemented to affect an appropriate vasoregulation in the pregnant animal and to promote adequate nutrient flow to the fetus.

Inhibiting Labor

As illustrated in FIG. 9A, FIG. 9B, FIG. 9C, FIG. 9D, FIG. 9E, FIG. 9F and 10, IGF-I is effective in inhibiting placental prostaglandin F and thromboxane production by the placenta. Thus, by regulating the concentrations of intra-uterine IGF-I levels, either by altering its production, its metabolism, its binding proteins and/or its direct administration or inhibition, the production of $PGF_{2\alpha}$ and $TxB_2$ can be altered, leading either to increased or decreased vaso-constriction and/or uterine contractility as desired. Thus, increasing IGF-I may be used to inhibit labor or vaso-constriction. Therefore, IGF-I treatment could be used to inhibit labor through its affects on vasoconstriction prostanoids.

As part of a method for inhibitive labor in a pregnant human IGF-I may be injected intra-amniotically (83 micrograms in 5 ml of 10 mM Hepes, 1 mM DTT, pH 7.4) into a pregnant animal having a gestational age of at least about 20 weeks, in humans. The standard dose to an average pregnant human female would be a dose sufficient to achieve a concentration of between 70 $\mu$g and 90 $\mu$g micrograms in the amniotic fluid or cord blood. For example, an intra-amniotic dose of between about 5 ng and 10 ng would be expected to provide such a concentration based on an average amniotic fluid volume of 1 liter. The most preferred mode of administration would therefore be intra-amniotically to achieve sufficient concentrations. However, other routes of administration are contemplated to be equally efficacious. Such dose would be expected to inhibit labor in a treated pregnant human and would be employed to prevent premature termination of gestation in pregnant patients having a gestational age of between about 20–36 weeks.

Inducing Labor

According to one proposed embodiment, labor may be induced by inhibiting or reducing the concentrations of IGF-I in a pregnant animal. In humans, such a therapy would be desirable in females of greater than 40 weeks gestational age. Examples of inhibitors of IGF-I are antibodies having specific binding affinity for IGF-I, as described in Example 8. The most preferred mode of administration is contemplated to be by intra-amniotic injection or by intra-uterine vein administration. Other intravenous routes, as well as intramuscular administration, could also be employed.

Clinical treatment techniques well known to those of skill in the obstetrical arts would be used together with the disclosure of the present invention in either inducing or inhibiting labor, as well as in treating hypertension in the pregnant animal, according to the present invention.

EXAMPLE 11

PLACENTAL PROSTANOID RESPONSE TO IGF-1 IN IUGR PREGNANCIES

Decreased levels of IGF-1 in association with intrauterine growth retardation have been reported in animal models (Bernstein et al., 1991; Straus et al., 1991; Jones et al., 1988) and in humans. IGF-1 levels in human umbilical cord blood have been correlated with birth weight (Wang et al., 1991; Verhaeghe et al., 1991). In addition, human decidual explant cultures from pregnancies complicated by IUGR have demonstrated decreased IGF-1 production (Heffner et al., 1992).

In this Example the release of thromboxane and prostacyclin in response to IGF-1 from the placenta in term pregnancies complicated by severe intrauterine growth retardation (IUGR) and without hypertension, compared with placentas from normal, uncomplicated term pregnancies was investigated.

A. MATERIALS AND METHODS

1. Patient selection

For the study group with intrauterine growth retardation (N=5), human placentas were used for parturients with term infants of birth weight below the 5th percentile for gestational age, based on population-specific parameters and menstrual dating confirmed by ultrasound in the first or second trimester. Exclusion criteria were as follows: 1) hypertensive disease, either acute or chronic, or pre-existing vascular disease; 2) gestational or pre-gestational diabetes; 3) fetuses with congenital anomalies, aneuploidy, or gross placental anomalies; 4) known or suspected intrauterine infection; 5) multiple gestations. For the control group, human term placentas were obtained from patients (N=3) without known material or fetal diseases with birth weights between the tenth to the 90th percentile. Patients who had received treatment with corticosteroids or non-steroidal anti-inflammatory agents were excluded from both groups. Tissues were obtained in accordance with the Institutional Review Board.

2. Placental perifusion

Fresh placentas were treated as described in Example 2. Each chamber was perifused with Medium 199 containing 0.05% bovine serum albumin, 100 ug/ml penicillin, 100 ug/ml streptomycin, 200 ng/ml estradiol, 2000 ng/ml progesterone, 100 U/ml insulin and $10^{-8}$M dexamethasone, hereafter in this Example, collectively referred to as Medium 199. Influx medium was aerated with 95% air and 5% carbon dioxide throughout the perifusion. Flow rate of the medium was 6 ml/hr for 10 hours.

Perifusion was performed with Medium 199 for five hours prior to treatment with IGF-1 in order to equilibrate the tissues. Ten minutes (transit time to fill chambers) before the fifth hour of perifusion (zero treatment time), Medium 199 was changed to Medium 199 containing IGF-1 at the following concentrations: 0 (control), 5.2, 10.4, 20.8 and 83.3 ng/ml (0.7 through $11 \times 10^{-9}$ molar). Three replicate chambers were perifused with each dose of IGF-1 at a rate of 6 ml/hr. and samples were collected every 30 minutes into 12×75 glass tubes containing 0.3 ml indomethacin (1100 ug/ml in dimethyl sulfoxide) and 0.1 ml bacitracin (300 U/ml). Collection of the effluent of the chambers was done simultaneously, using an ISCO fraction collector Retriever III adapted with rack and manifold. Samples were stored at −20° C. until assays were performed. This experimental design was performed five times, with placental tissues from different patients meeting the above study group criteria. Three placentas from women with term, uncomplicated pregnancies were also perifused in this fashion and used as normal controls.

3. Prostanoid radioimmunoassays

Because prostanoid recovery and stability in this system were nearly 100%, as experimentally determined and as reported previously (Harper et al., 1983), no data correction for procedural losses was done. Radioimmunoassays were performed in a manner similar to that previously described (in Example 1 and Kang and Siler-Khodr, 1993). The prostanoid release of each of the samples collected from hour 4.5, 5, 6, 7, 8, 9 and 10 was determined. All the samples from a given perifusion (placenta) were determined in the same assay. All other materials and methods were as described in Examples 1 and 2.

4. Statistical analysis

As with previous Examples, the release of $TxB_2$ and 6-keto-$PGF_{1\alpha}$ from a given chamber was related to its functional competence rather than the media volume or tissue weight. This was done by normalizing each chamber's prostanoid release at each time point to its own release at hour 5 (i.e., the zero treatment time). Expressing each chamber's response in relation to its functional competence at the start of treatment results in very low variance in the response of the replicated chambers.

For both $TxB_2$ and 6-keto-$PGF_{1\alpha}$, the normalized release from each chamber for each of the IUGR placentas and for the controls, at each dose of IGF-1 and at each time point, was calculated. The effect of IGF-1 was then determined by expressing the prostanoid release from the treated chambers as a percent of the mean release of the chamber without IGF-1 treatment for that placenta at each time point. Thus, the average release for untreated chambers for each IUGR placenta and for the normals was 100%. The mean (±SEM) response to each dose of IGF-1 at each time point for each placenta, IUGR and the normals was calculated.

Three-way analysis of variance, dose of IGF-1 versus time, was used to determine different response patterns among the five IUGR placentas and the normals. The data for $TxB_2$ or 6-keto-$PGF_{1\alpha}$ was first tested for homogeneity using Bartlett's test; however, log transformation was not necessary. The cumulative effect of differing doses of IGF-1 on prostanoid release over the five hours of treatment was also analyzed using two-way analysis of variance comparing IUGR placentas to normals across the IGF-1 dose. Two-way analysis of variance was also used to determine the effect of different doses of IGF-1 across time in each placenta. When a significant interaction was observed, one-way analysis of variance and Student-Neuman-Keuls test were used to determine the point(s) that differed significantly (P<0.05).

In addition, the percent change of $TxB_2$ from zero treatment time to the fifth hour of treatment as compared to that for 6-keto-$PGF_{1\alpha}$ for each chamber was calculated as a ratio. Statistical differences were determined by two-way analysis of variance for the normal group and the IUGR placentas across each dose of IGF-1 studied.

B. RESULTS

Table 2 lists the clinical characteristics of the IUGR group. None of these patients had hypertension or vasculopathy, none were smokers, and none of the infants had congenital malformations or clinical evidence of abnormal genetic syndromes. The control group consisted of three normal term pregnancies with birth weights from the tenth to 90th percentile and no evidence of maternal or fetal disease.

TABLE 2

Clinical characteristics of the IUGR group.

| Patient | Gestational age (weeks | Mode of delivery | Birth weight (g) | Placental weight (g) |
|---|---|---|---|---|
| A | 40 | SVD | 2623 | 352 |
| B | 40 | SVD | 2554 | 372 |
| C | 37 | C/S | 2120 | 280 |
| D | 40 | SVD | 2393 | 310 |
| E | 38.8 | SVD | 1883 | 220 |

SVD = vaginal delivery
C/S = caesarean section

Figures 12A, 12B:
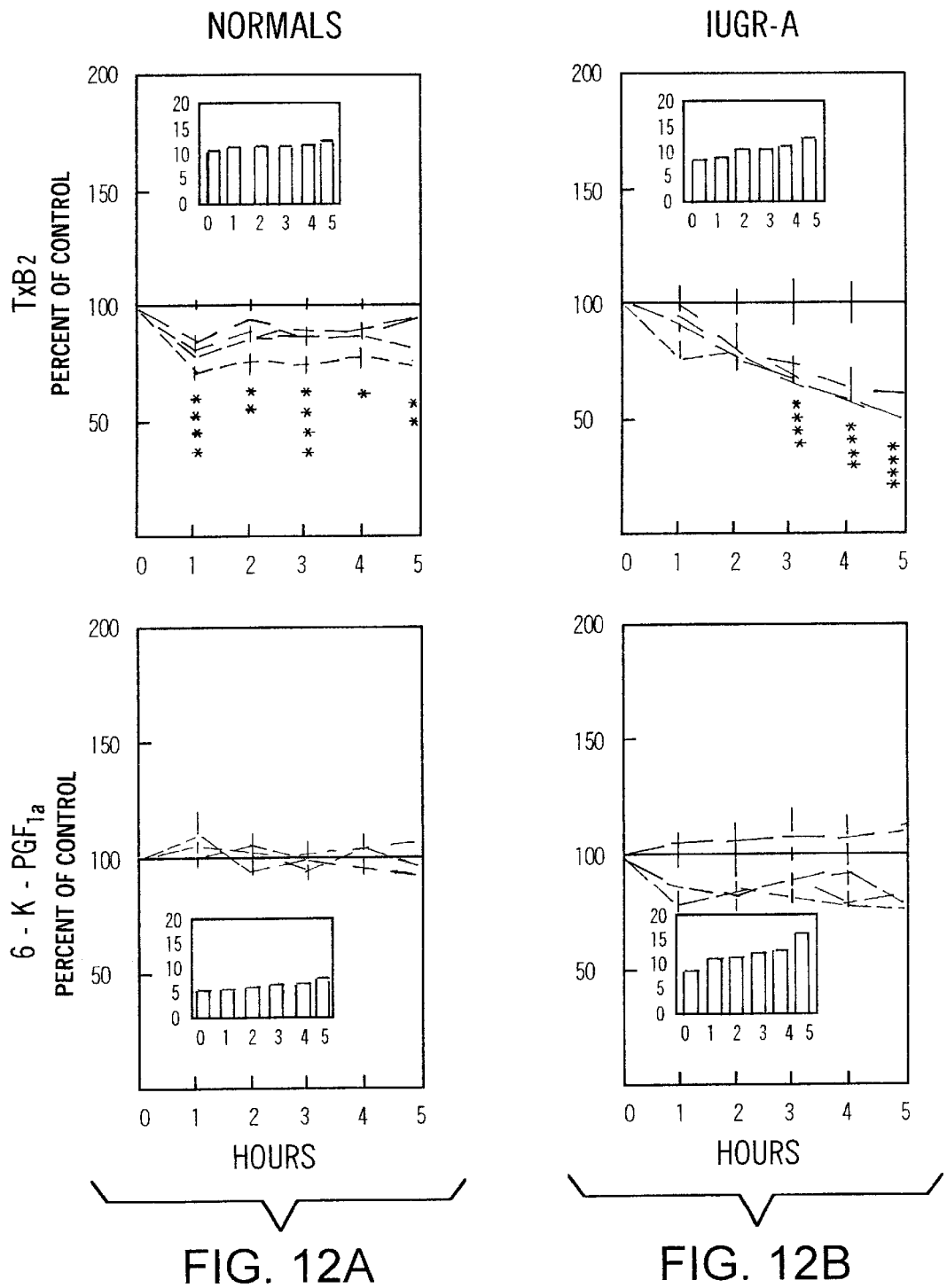
FIG. 12A. Prostanoid release in normal placentas. The dose-related $TxB_2$ release and the dose-related 6-keto-$PGF_{1\alpha}$ release, in response to varying doses of IGF-1 from hour 5 through hour 1–10 of perifusion, normalized to the zero treatment time, is shown [control (—); 5.2 ng/ml (—0—); 10.4 ng/ml (—▽—); 20.8 ng/ml (__△__) and 83.3 ng/ml (—□—)]. Inserts show five hour basal prostanoid release in ng/g/hr.
FIG. 12B. Prostanoid release in the IGF-1 responsive group, Placenta A. The dose-related $TxB_2$ release and the dose-related 6-keto-$PGF_{1\alpha}$ release, in response to varying doses of IGF-1, normalized to the zero treatment time, is shown [control (—); 5.2 ng/ml (—0—); 10.4 ng/ml (—▽—); 20.8 ng/ml (__△__) and 83.3 ng/ml (—□—)]. The normal placentas (mean±SEM) in FIG. 12A are compared with IGF-1 response IUGR placentas A. Significant differences are noted ($^*p<0.05$). Inserts show five hour basal prostanoid release in ng/g/hr.
Figures 12C, 12D:
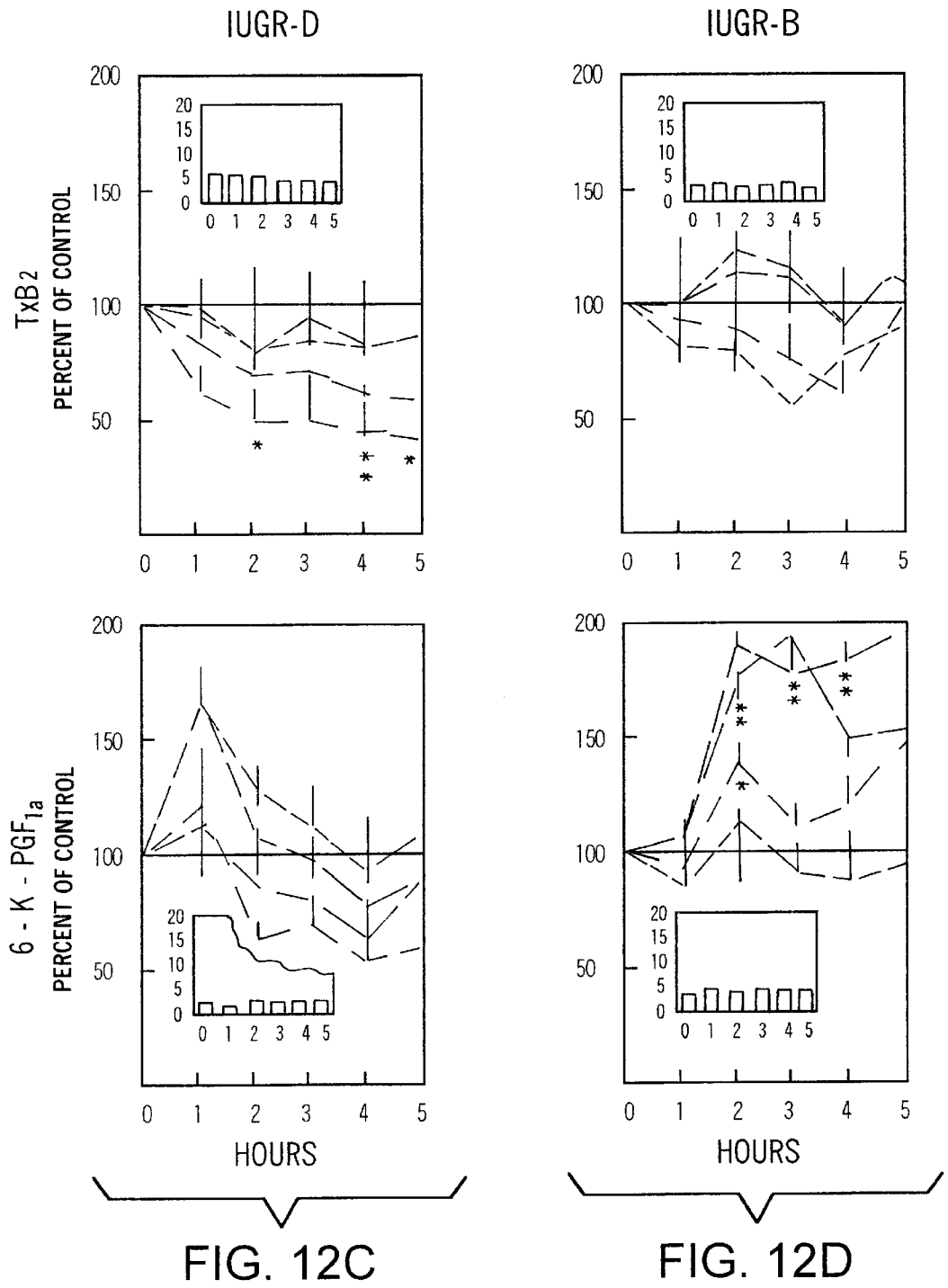
FIG. 12C. Prostanoid release in the IGF-1 responsive group, Placenta D. The dose-related $TxB_2$ release and the dose-related 6-keto-$PGF_{1\alpha}$ release, in response to varying doses of IGF-1, normalized to the zero treatment time, is shown [control (—); 5.2 ng/ml (—0—); 10.4 ng/ml (—▽—); 20.8 ng/ml (__△__) and 83.3 ng/ml (—□—)]. The normal placentas (mean±SEM) in FIG. 12A are compared with IGF-1 response IUGR placentas D. Significant differences are noted ($^*p<0.05$). Inserts show five hour basal prostanoid release in ng/g/hr.
FIG. 12D. Prostanoid release in the IGF-1 responsive group, Placenta B. The dose-related $TxB_2$ release and the dose-related 6-keto-$PGF_{1\alpha}$ release, in response to varying doses of IGF-1, normalized to the zero treatment time, is shown [control (—); 5.2 ng/ml (—0—); 10.4 ng/ml (—▽—); 20.8 ng/ml (__△__) and 83.3 ng/ml (—□—)]. The normal placentas (mean±SEM) in FIG. 12A are compared with IGF-1 response IUGR placentas B. Significant differences are noted ($^*p<0.05$). Inserts show five hour basal prostanoid release in ng/g/hr.

The response of placental release of $TxB_2$ and 6-keto-$PGF_{1\alpha}$ over five hours of perifusion in response to varying concentrations of IGF-1 differed among the IUGR placentas. The IUGR placental response for TxB2 was found to fall into one of two patterns. One group—placentas A, D and B (the responders)—exhibited an inhibition of $TxB_2$ as do normal placentas. The non-responders—placentas C and E—did not demonstrate inhibition of $TxB_2$ release following treatment with IGF-1. FIG. 12A, FIG. 12B, FIG. 12C. FIG. 12D, FIG. 13A, FIG. 13B and FIG. 13C illustrate the effect of IGF-1 on $TxB_2$ and 6-keto-$PGF_{1\alpha}$ for the responders and non-responders respectively, as a percent change from the mean release for their control chambers (no IGF-1) over time. The basal release (ng/g of placental tissue/hour) for each of the IUGR placentas and the normals is shown in the inserts. In FIG. 14A and FIG. 14B, the five hour cumulative response of $TxB_2$ and 6-keto-$PGF_{1\alpha}$ for each dose of IGF-1 studied in the normal and IUGR placentas is compared.

1. Prostanoid release in the IGF-1 responsive group:

In the normal placentas a dose-related suppression of $TxB_2$ with increasing concentration of IGF-1 was observed, whereas 6-keto-$PGF_{1\alpha}$ was not affected by IGF-1 (FIG. 12A). The IUGR placentas A, D and B also responded to IGF-1 with an inhibition of $TxB_2$ release (FIG. 12B, FIG. 12C and FIG. 12D). In two of these placentas, A and D, 6-keto-$PGF_1$ a was unchanged as in normals, but in IUGR placenta B there was a significant increase in this vasodilator following the lower doses of IGF-1 (FIG. 12D).

In IUGR placenta A, a significant suppression of $TxB_2$ was observed at every dose of IGF-1 from the third through the fifth hour or treatment, while there was no change in 6-keto-$PGF_{1\alpha}$. The inhibition of $TxB_2$ after five hours of exposure to IGF-1 was greater than that of the normal placentas. The five hour cumulative release of TxB2 was significantly inhibited by IGF-1 at every dose tested, and this suppression was greater than the inhibition for normal placentas at the concentrations of IGF-1 (FIG. 14A).

For IUGR placenta D there was a dose-related suppression of $TxB_2$, which was significant at hours two, four, five using 83.3 mg/ml of IGF-1. Once again, after five hours of exposure to IGF-1, a significantly greater inhibition of $TxB_2$ was observed compared with the normal placentas. The five hour cumulative response was significantly inhibited at each dose of IGF-1 and this suppression was greater than the inhibition for normal placenta at the lower doses. A significant isolated decrease in 6-keto-$PGF_{1\alpha}$ was observed at the second hour with IGF-1 (83.3 ng/ml); however, the five hour cumulative response was not affected by these concentrations of IGF-1, as in the normal placentas.

IUGR placenta B also responded to IGF-1 with a significant inhibition of $TxB_2$, but this occurred only at the higher concentrations (20.8 and 83.3 ng/ml) after three hours of exposure to IGF-1. The five hour cumulative response was significantly inhibited at the higher concentration, and this was similar to the response in the normal placentas. Interestingly, 6-keto-$PGF_1$ a was significantly increased at the lower doses of IGF-1. The five hour cumulate response of 6-keto-$PGF_1$ a was significantly increased using 5.2 and 10.4 ng/ml concentration of IGF-1, and this response was significantly different from that observed in normal placentas in which no change in IGF-1 at any dose was observed (FIG. 14A).

The $TxB_2$ or the 6-keto-$PGF_{1a}$ responsiveness of these IUGR placentas to IGF-1 could not be predicted by the basal release of these prostanoids. As shown in the inserts, in one case (placenta A) these basal prostanoid releases were similar to that observed in normal placentas, whereas in placentas D and E they were significantly lower.

Figure 13A:
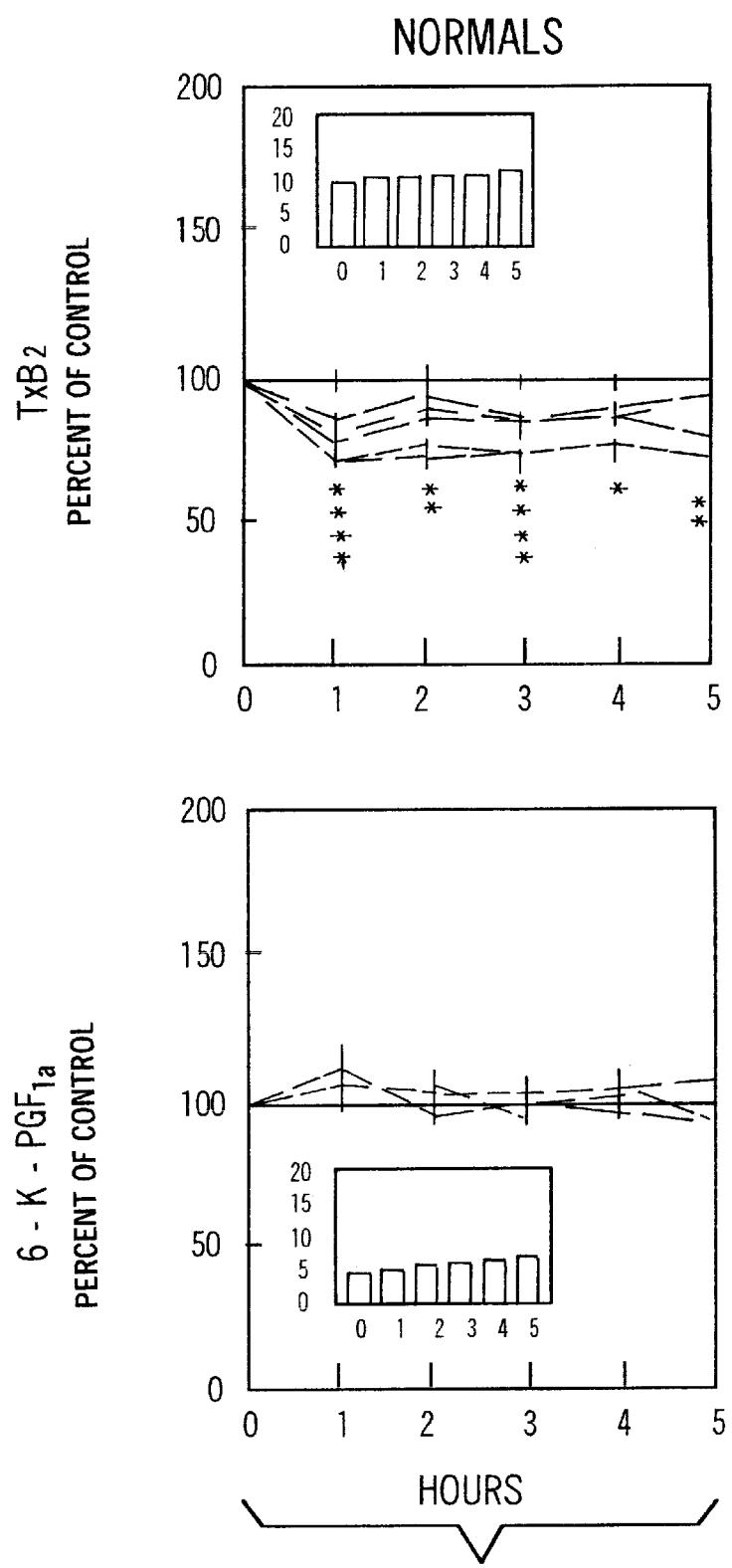
FIG. 13A. Prostanoid release in normal placentas (also see FIG. 12A). The dose-related $TxB_2$ release and the dose-related 6-keto-$PGF_{1\alpha}$ release, in response to varying doses of IGF-1from hour 5 through hour 1–10 of perifusion, normalized to the zero treatment time, is shown [control (—); 5.2 ng/ml (—0—); 10.4 ng/ml (—▽—); 20.8 ng/ml (__△__) and 83.3 ng/ml (—□—)]. Inserts show five hour basal prostanoid release in ng/g/hr.
Figure 13B:
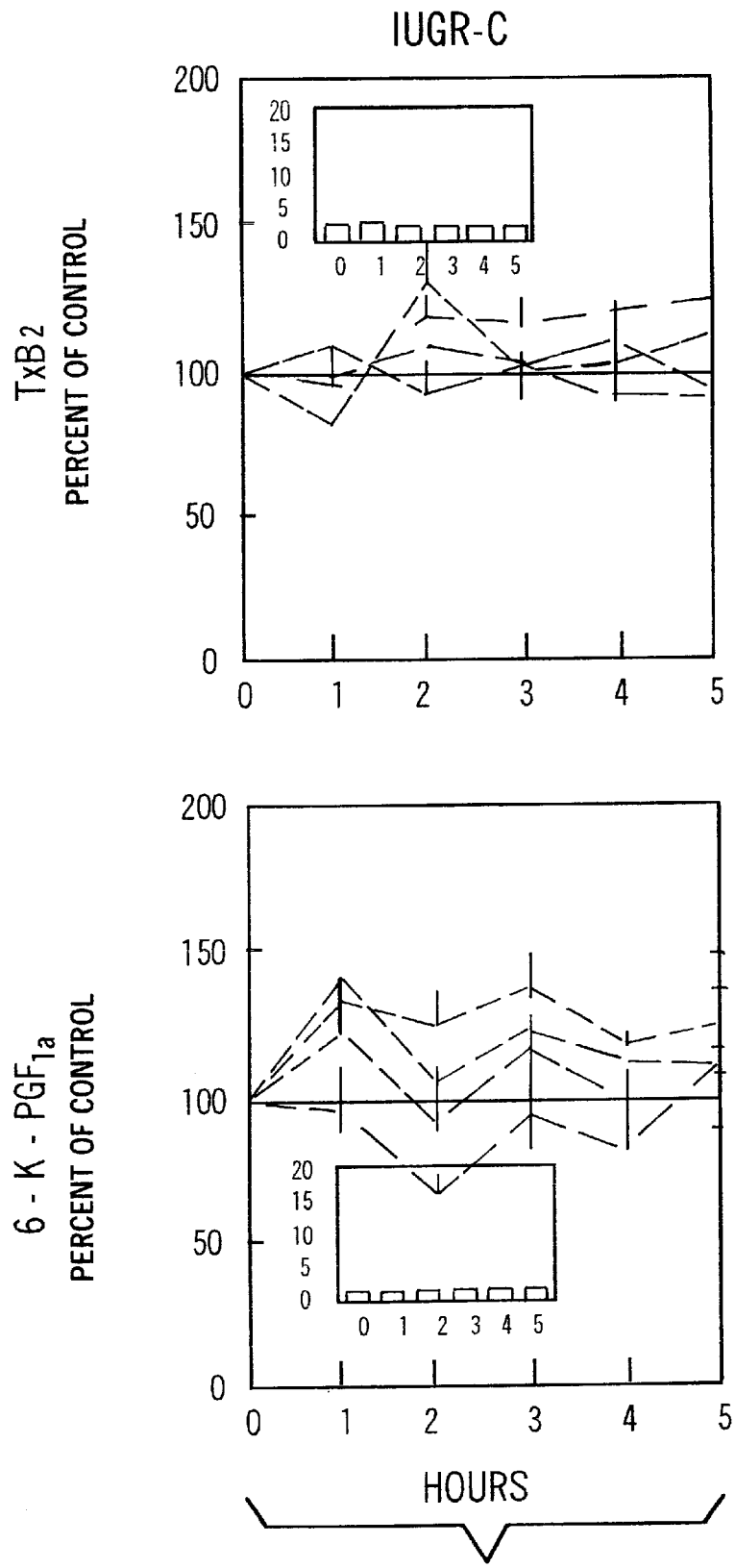
FIG. 13B. Prostanoid release in the IGF-1 non-responsive group, Placenta C. The dose-related $TxB_2$ release and the dose-related 6-keto-$PGF_{1\alpha}$ release, in response to varying doses of IGF-1, normalized to the zero treatment time, is shown [control (—); 5.2 ng/ml (—0—); 10.4 ng/ml (—▽—); 20.8 ng/ml (__△__) and 83.3 ng/ml (—□—)]. The normal placentas (mean±SEM) in FIG. 12A are compared with IGF-1 response IUGR placentas C. Significant differences are noted ($^*p<0.05$). Inserts show five hour basal prostanoid release in ng/g/hr.
Figure 13C:
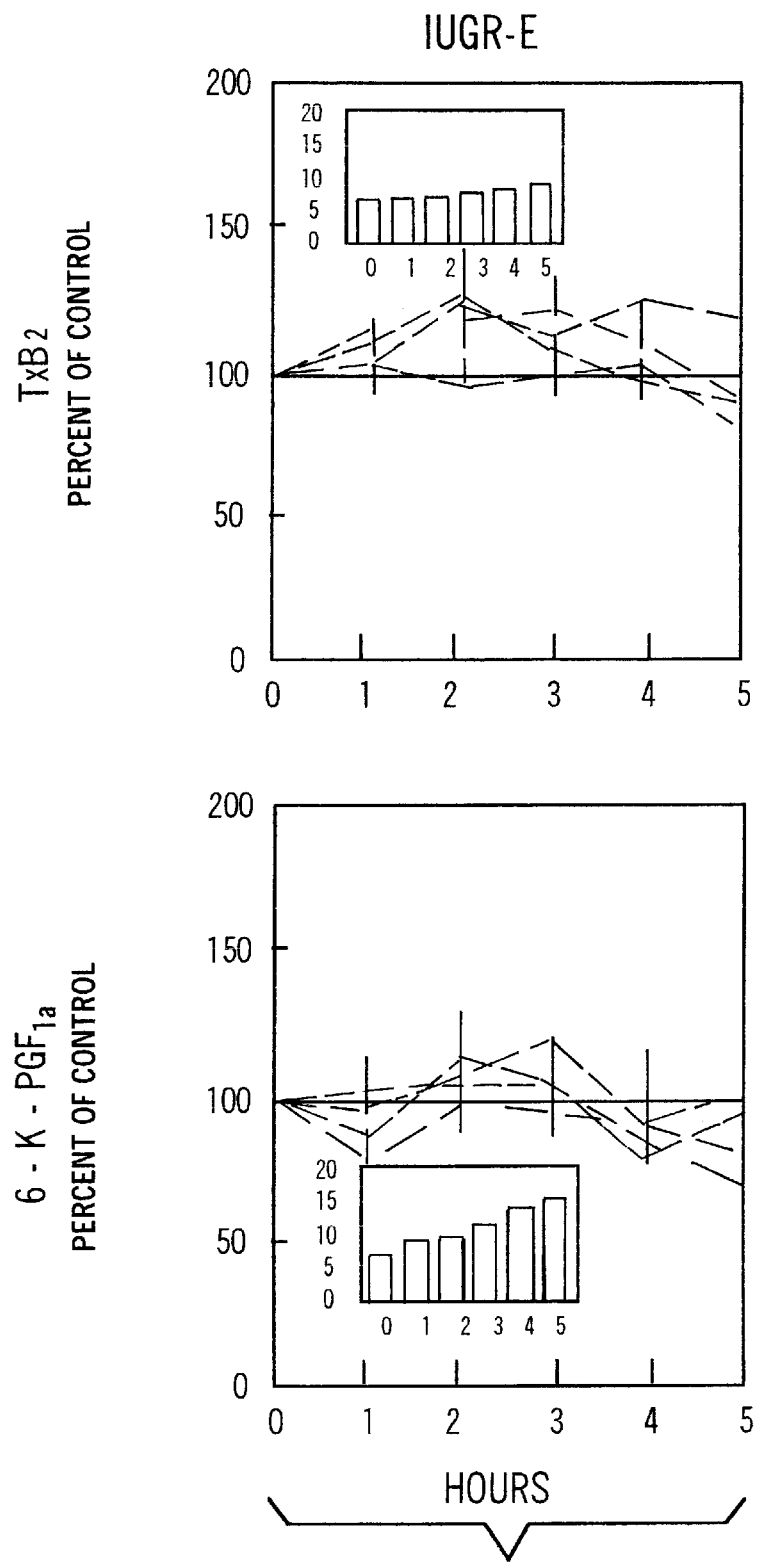
FIG. 13C. Prostanoid release in the IGF-1 responsive group, Placenta E. The dose-related $TxB_2$ release and the dose-related 6-keto-$PGF_{1\alpha}$ release, in response to varying doses of IGF-1, normalized to the zero treatment time, is shown [control (—); 5.2 ng/ml (—0—); 10.4 ng/ml (—▽—); 20.8 ng/ml (__△__) and 83.3 ng/ml (—□—)]. The normal placentas (mean±SEM) in FIG. 12A are compared with IGF-1 response IUGR placentas E. Significant differences are noted ($^*p<0.05$). Inserts show five hour basal prostanoid release in ng/g/hr.
Figure 14A:
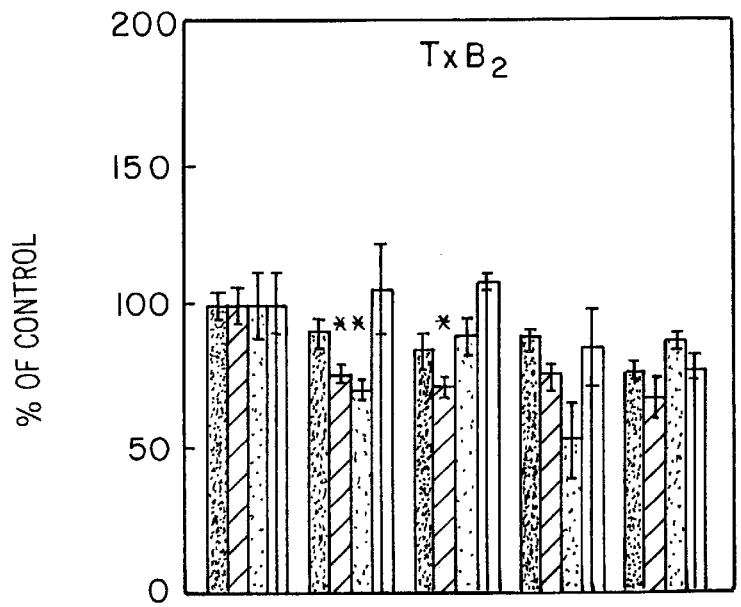
FIG. 14A. The five hour cumulative $TxB_2$ and 6-keto-$PGF_{1\alpha}$ responses to varying doses of IGF-1 are shown in the normals [filled] and in IUGR responsive placentas A [diagonal lines]; D [totally shaded]; and B [open].
Figure 14A:
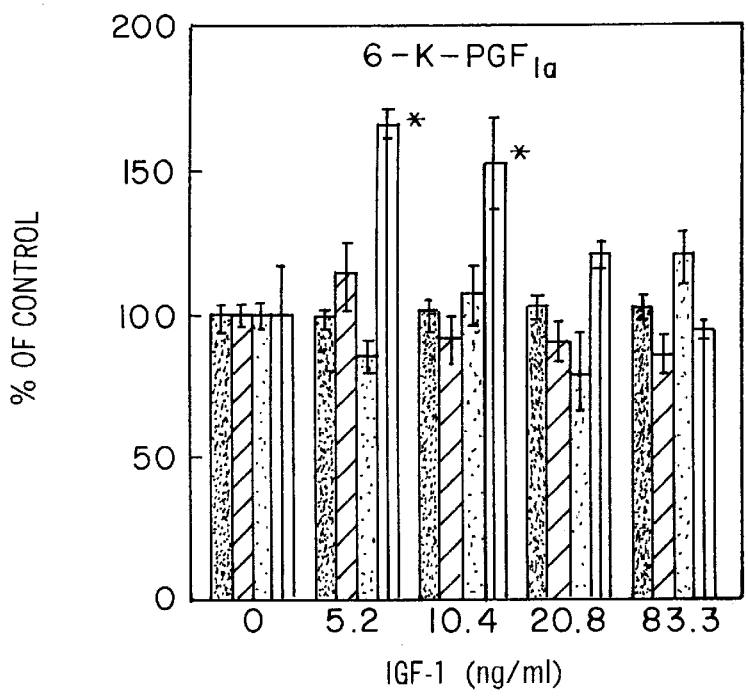
Figure 14B:
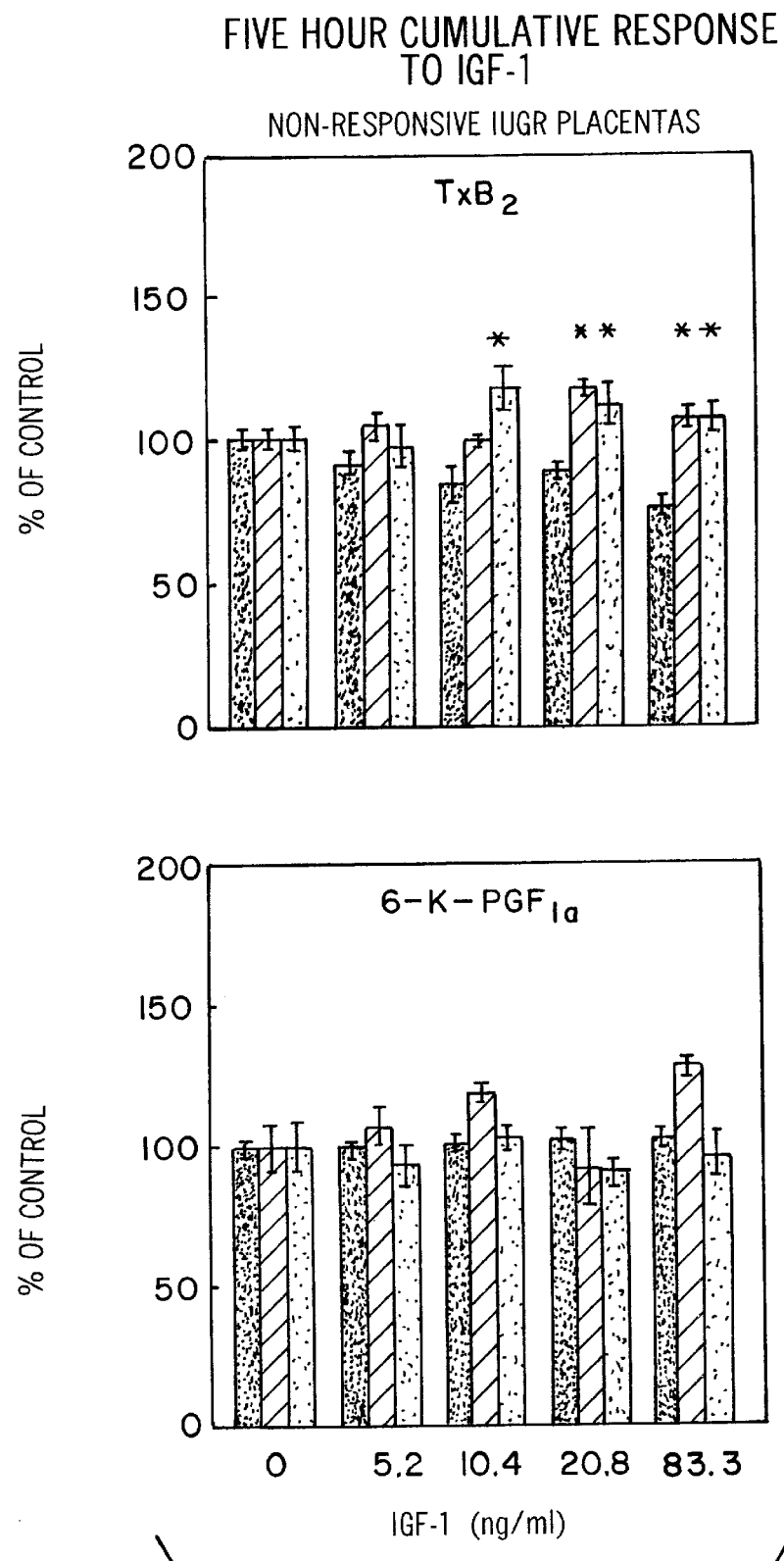
FIG. 14B. The five hour cumulative $TxB_2$ and 6-keto-$PGF_{1\alpha}$ responses to varying doses of IGF-1 are shown in the normals [filled] and in IUGR non-responsive placentas C [diagonal lines] and E [totally shaded]. Significant differences are noted ($^*p<0.05$).

2. Prostanoid release in the non-responsive group:

FIG. 13A, FIG. 13B and FIG. 13C illustrates the absent $TxB_2$ response over five hours of incubation with varying doses of IGF-1 in IUGR placentas C and E as compared to controls. This pattern of response was significantly different from that in normal placentas throughout the experimental period. The five hour cumulative response of $TxB_2$ to IGF-1 for either placenta C or E did not differ from their untreated controls, and this finding was significantly different from that of the normal placentas in which $TxB_2$ production was inhibited (FIG. 14B).

In IUGR placentas C and E, IGF-1 did not significantly affect the release of 6-keto-$PGF_{1a}$ at any dose studied. This finding was similar to that for the normal placentas. The cumulative release of 6-keto-$PGF_{1a}$ in these IUGR placentas was also unaltered by IGF-1 as in the normal placentas.

As with the responsive group, the IGF-1 non-responsive IUGR placentas could not be predicted by the basal release of these prostanoids. As is shown in the inserts, in one case (placenta C) these basal prostanoid releases were very low compared to normal placentas, whereas in placenta E they were similar to those of the normals.

Figure 15A:
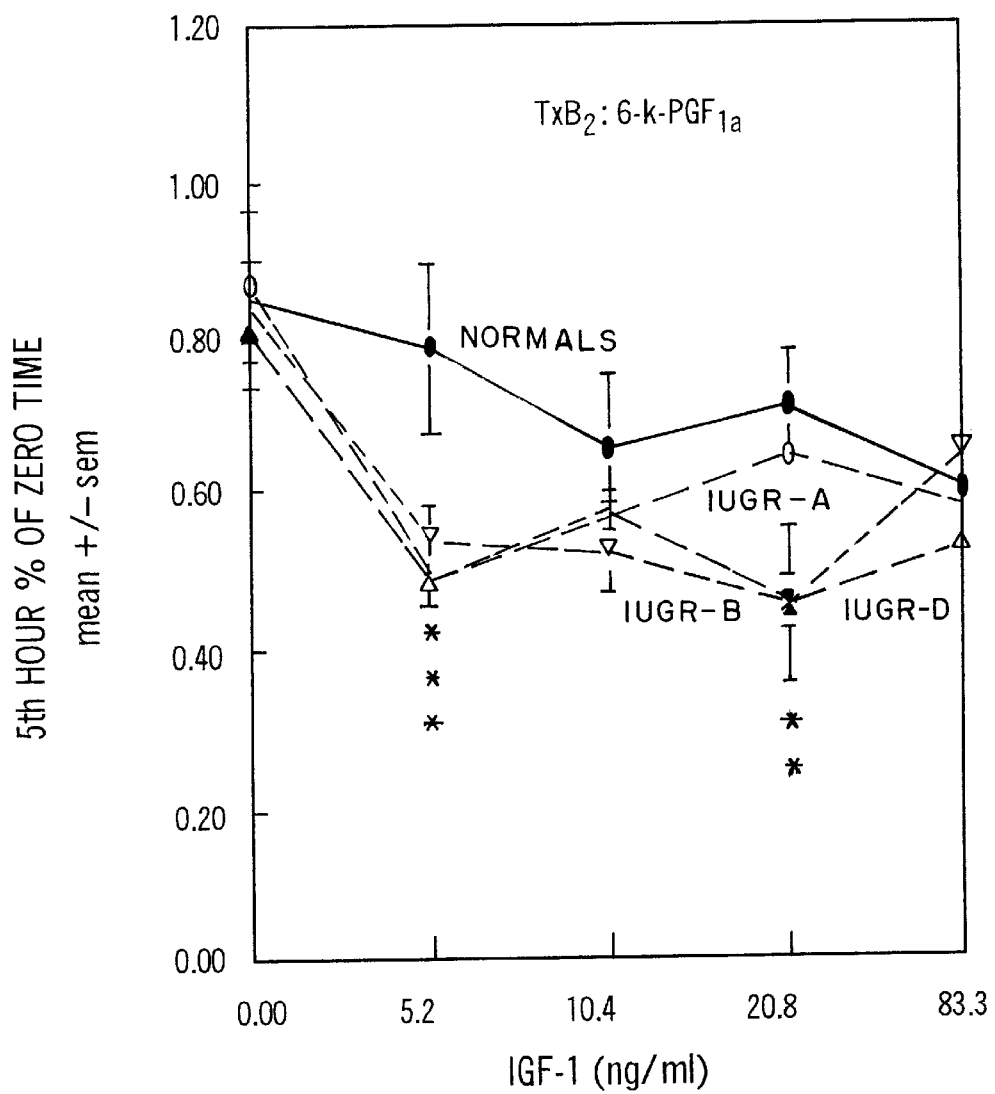
FIG. 15A. The ratio (mean±SEM) of vasoconstrictor to vasodilator ($TxB_2$ to 6-keto-$PGF_{1\alpha}$) production after the fifth hour of treatment for normal placentas, responsive IUGR placentas A, D, and B is shown.
Figure 15B:
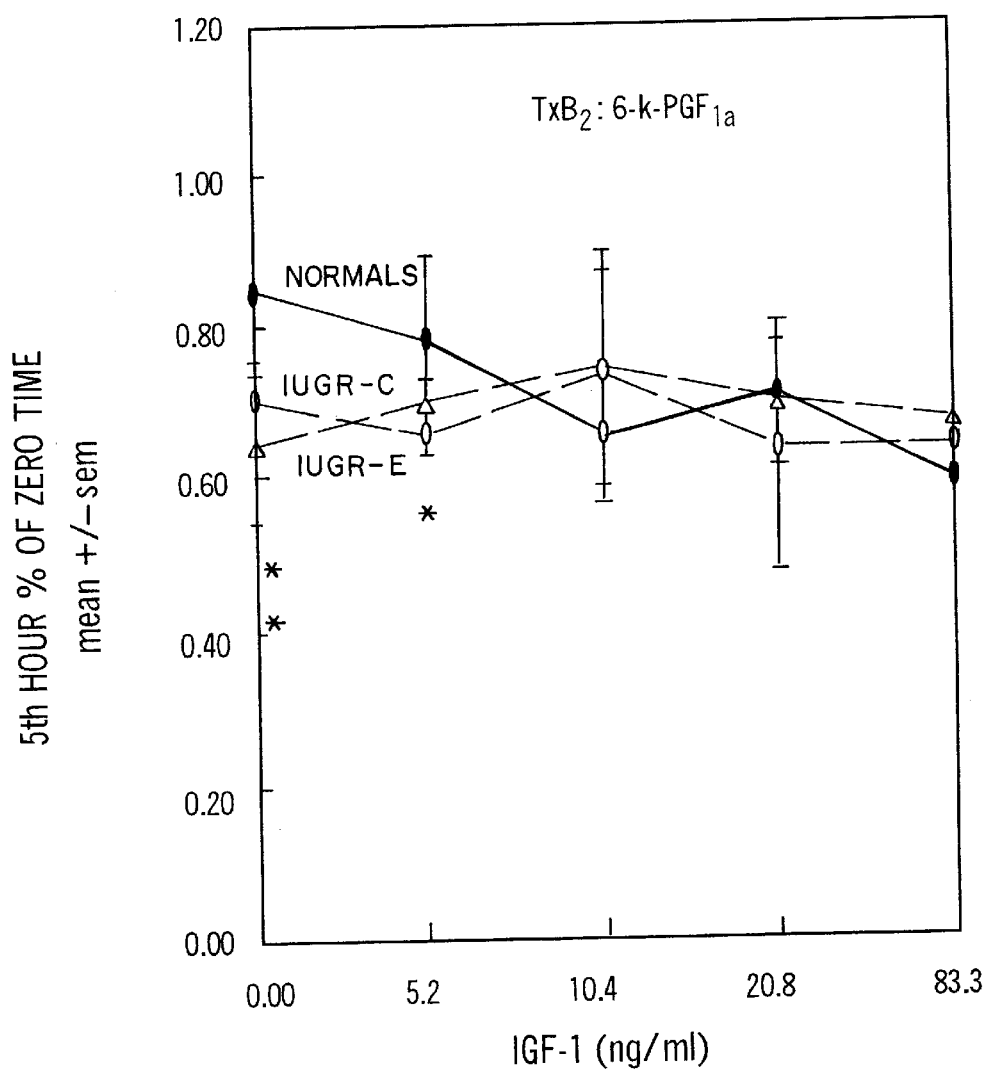
FIG. 15B. The ratio (mean±SEM) of vasoconstrictor to vasodilator ($TxB_2$ to 6-keto-$PGF_{1\alpha}$) production after the fifth hour of treatment for normal placentas, and non-responsive IUGR placentas C and E is shown. The non-responsive IUGR placentas, C and E, exhibit a significantly suppressed ratio at the zero dose and show no further decrease in this ratio in response to IGF-1 ($^*p<0.05$).

3. Ratio of vasoconstrictor to vasodilator ($TxB_2$;6-keto-$PGF_{1a}$):

In order to investigate a possible effect of IGF-1 on vasoregulation, the inventor determined the ratio of $TxB_2$, a vasoconstrictor, to 6-keto-$PGF_a$, a vasodilator. No significant difference between normals, responsive and non-responsive IUGR placentas at any dose of IGF-1 doses was observed (FIG. 15A and FIG. 15B). However, when the change of $TxB_2$ production from zero time to the fifth hour of treatment was compared to that for 6-keto-$PGF_1$a and expressed as a ratio, significant differences between the normals, IUGR responsive and IUGR non-responsive placentas were observed. The change from the zero time to the fifth hour of testing for the ratio of $TxB_2$ to 6-keto-$PGF_{1a}$ was similar in the untreated, control chamber of the normal placentas and the IGF-1 responsive IUGR placentas. However, this ratio in the untreated control chamber of the non-responsive IUGR placenta was significantly less than that for either the normal or the IUGR responsive placentas. In addition, in the IUGR responsive placentas, this ratio was very sensitive to IGF-1, i.e., even low doses of IGF-1 enhanced the vasodilators much more readily than in normal placentas. As the dose of IGF-1 increased in the normal placentas, the change in vasoconstrictor to vasodilator production became similar to that for the IUGR responsive placentas. In the non-responsive group this ratio did not change with any dose of IGF-1. It is noteworthy that the basal ratio was already similar to that for the normals incubated with the higher doses of IGF-1 (10.4–83.3 ng/ml).

IUGR may be the result of a variety of insults to the feto-placental unit resulting in restricted fetal growth. Constitutionally small fetuses and uncertainty in dating some pregnancies may complicate the diagnosis of IUGR. In this study, only fetuses with confirmed menstrual dating and birth weight less than the fifth percentile were included to minimize inclusion of the "normal" small gestation. Even when specific fetal factors are excluded, maternal factors may contribute to decreased uteroplacental perifusion. Because fetuses with IUGR in a pregnancy with hypertension may be exposed to a different hormonal milieu than those in pregnancies complicated by pre-eclampsia, those pregnancies were also excluded. By excluding patients with hypertension, the inventor attempted to avoid the influences of pre-eclampsia on placental prostanoid production.

In this study of placental tissue from pregnancies complicated by severe intrauterine growth retardation without hypertension, the prostanoid response to IGF-1 could be divided into two subgroups. In three of the five study group placentas (the responsive group) inhibition of thromboxane was observed. Even at low doses, a favorable effect (i.e., decrease) of the ratio of vasoconstrictor to vasodilator was observed. The inhibition of $TxB_2$ was significantly greater than the normally responsive controls by the fifth hour of treatment. The inventor observed a trend of enhanced sensitivity to IGF-1 compared with controls at the intermediate doses; however, at the highest dose, the change in the ratio of $TxB_2$ to 6-keto-$PGF_{1a}$ approximately 55–65%, was the same as controls.

The second group of IUGR placentas demonstrated insensitivity to IGF-1 and no significant change in the vasoconstrictor to vasodilator ratio over time compared with normals. Clinical characteristics or basal prostanoid releases were not helpful in distinguishing responders from non-responders. It is possible that the dose required to elicit a response is higher than the highest dose tested. However, in the control chambers of the non-responsive IUGR placentas, the ratio of $TxB_2$ to 6-keto-$PGF_{1a}$ was already significantly lower than that for normals or responsive IUGR placenta before treatment. IGF-1 did not decrease further this ratio, suggesting a prior exposure to IGF-1 or insensitivity to it.

This study demonstrates that at least 50% of placentas from pregnancies complicated by intrauterine growth retardation respond to IGF-1 by decreasing the ratio of thromboxane to prostacyclin. Thus, this specific regulation of placental enzymes involved in thromboxane production by IGF-1, may be a mechanism to influence uteroplacental blood flow and hence promote intrauterine growth. This response does not appear to be related to basal prostanoid release, as placentas with normal, as well as low, basal prostanoid production could respond by decreasing thromboxane and demonstrating a decreased thromboxane to prostacyclin ratio. However, the response may be related to prior IGF-1 exposure or insensitivity.

EXAMPLE 12

EFFECT OF IGF-I ON PLACENTAL THROMBOXANE IN PREGNANCY-INDUCED HYPERTENSION

The present example demonstrates that the administration of IGF-I inhibits thromboxane in placental tissue from subjects having pregnancy-induced hypertension.

Thromboxane causes vasoconstriction and has been shown to be elevated or to have an abnormally increased ratio to $PGI_2$ in pregnancy-induced hypertension, and thereby is a contributing factor to pregnancy-induced hypertension.

Figure 16:
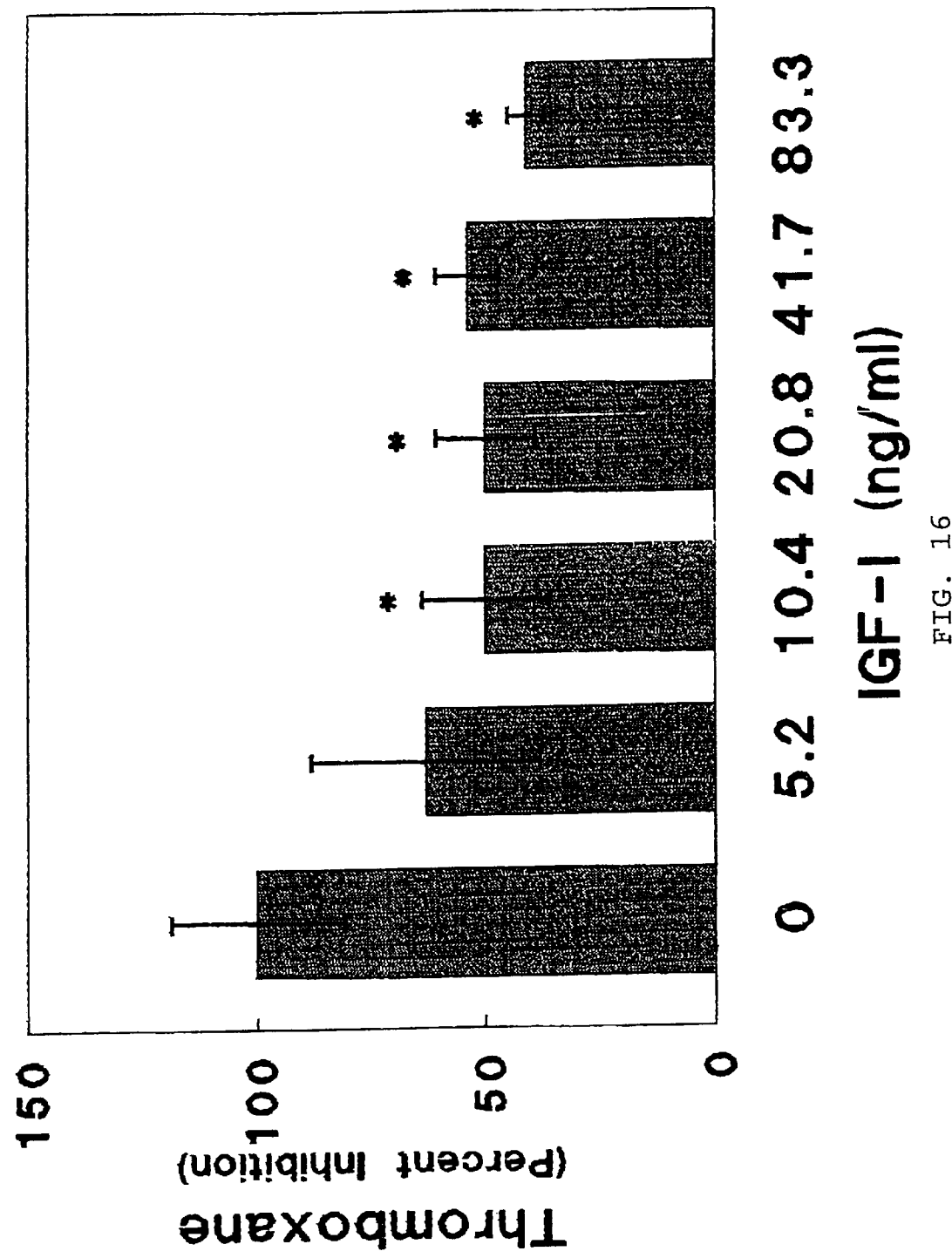
FIG. 16 demonstrates the percent inhibition of thromboxane versus incureasing concentrations of IGF-I in pregnancy-induced hypertension.

A placenta was obtained from a patient having pregnancy-induced hypertension and, using triplicate chambers for each dose, the dose-related action of IGF-I on placental thromboxane release was studied in a similar manner to that described in Example 11. Assays for thromboxane were also carried out as described therein. FIG. 16 demonstrates the surprising and unexpected extent of inhibition of thromboxane in response to IGF-I in this placenta. One of skill in this art upon reading these results would realize that the administration of IGF-I would be an appropriate and effective treatment for pregnancy-induced hypertension.

The following references are specifically incorporated herein by reference in pertinent part for the purposes indicated herein and to demonstrate the state of the art.

REFERENCES

Angle M. J. & Johnston J. M., (1990), "Fetal tissues and autocoid biosynthesis in relation to the initiation of parturition and implantation," In *Uterine Function*, (Ed.) Carsten, M. E. & Miller, J. D. pp. 471–500, New York:Plenum Press.

Arias and Tomich, "Etiology and outcome of low birth weight and preterm infants," *Obstet. Gynecol.*, 60:277–281, 1982.

Bala et al., (1990), Characterization of the major phosphoinositide-specific phospholipase-C of human amnion, *Biology of Reproduction*, 43:704–711.

Bernstein et al., "Insulin-like growth factor in substrate-deprived, growth-retarded fetal rats," *Pediatr. Res.*, 30:154–157, 1991.

Demers, L. M & Gabbe, S. G. (1976), "Placental prostaglandin levels in preeclampsia," *American Journal of Obstetrics and Gynecology*, 126:137–139.

Duchesne et al., (1978), "Prostaglandin synthesis in human placenta and fetal membranes," *Prostaglandins*, 15:19–41.

Ekblad et al. (1987), "The effect of acute hypoxia on prostaglandin release in perfused human fetal placenta," *Prostaglandins*, 33:553–560.

Gibbs et al. (1988), "Cyclo-oxygenase products formed by primary cultures of cells from human chorion laeve: Influence of steroids," *Canadian Journal of Physiology and Pharmacology*, 66:788–793.

Haning et al. (1982), "Effects of dibutyryl cAMP, LHRH, and aromatase inhibitor on simultaneous outputs of prostaglandin $F_{2\alpha}$, and 13,14-dihydro-15-keto-prostaglandin $F_{2\alpha}$ by term placental explants," *Prostaglandins*, 23:29–40.

Harper et al. (1983), "Prostaglandin production by human term placentas in vitro," *Prostaglandins Leukotrienes and Medicine*, 11"121–129.

Heffner et al., "Secretion of prolactin and insulin-like growth factor by decidual explant cultures from pregnancies complicated by intrauterine growth retardation," *Am. J. Obstet. Gynecol.*, 167:1431–1436, 1992.

Hillier K. & Smith, M. D. (1981), "Prostaglandin E and F concentrations in placentae of normal, hypertensive and preeclamptic patients," *British Journal of Obstetrics and Gynaecology*, 88:274–277.

Jarabak J. (1972), "Human placental 15-hydroxy prostaglandin dehydrogenase," *Proceedings of the National Academy of Sciences USA*, 69:533–534.

Jogee et al. (1983), "Decreased prostacyclin production by placental cells in culture from pregnancies complicated by fetal growth retardation," *British Journal of Obstetrics and Gynaecology*, 90:247–250.

Jones et al., "Studies of the growth of fetal sheep. Effects of surgical reduction in placental size, or surgical manipulation of uterine blood flow on plasma sulphation promoting activity and on the concentration of insulin-like growth factors I and II," *J. Dev. Physiol.*, 10: 179–188, 1988.

Kang et al. (1991), "Dose-related action of GnRH on basal prostanoid production from the human term placenta," *American Journal of Obstetrics and Gynecology*, 165:1771–1776.

Khong et al., "Inadequate maternal response to placentation in pregnancies complicated by pre-eclampsia and by small-for-gestational-age infants," *Br. J. Obstet. Gynecol.*, 93:1049–1059, 1986.

Mitchell et al. (1978a), "Thromboxane $B_2$ and human parturition: Concentrations in the plasma and production in vitro," *Journal of Endocrinology*, 78:435–441.

Mitchell et al. (1978b), "Possible role for prostacyclin in human parturition," *Prostaglandins*, 16:931–937.

Mitchell et al. (1978c), "Specific production of prostaglandin E by human amnion in vitro," *Prostaglandins*, 15:377–382.

Mitchell et al. (1982), "The human placenta: A major source of prostaglandin $D_2$," *Prostaglandins Leukotrienes and Medicine*, 8:383–387.

Mitchell M. D. (1987), "Epidermal growth factor actions on arachidonic acid metabolism in human amnion cells," *Biochimica et Biophysica Acta*, 928:240–242.

Murphy et al. (1990), *Endocrine Reviews*, 11(3): 443–453.

Myatt L. (1990), "Placental biosynthesis, metabolism, and transport of eicosanoids," In *Eicosanoids in Reproduction*, (Ed.) Mitchell, M. D. pp. 169–197, Boston: CRC Press.

Myatt et al. (1983), "Regulation of prostacyclin metabolism in human placental cells in culture by steroid hormones. In: Lewis P. J. et al., eds. Prostacyclin in pregnancy. New York: Raven Press, 119–29.

Negro-Vilar et al. (1986), "Transmembrane signals mediating neural peptide secretion: Role of protein kinase C activators and arachidonic acid metabolites in luteinizing hormone-releasing hormone secretion," *Endocrinology*, 119:2796–2802.

Olson et al. (1983a), "Prostaglandin synthesis by human amnion is dependent upon extracellular calcium," *Canadian Journal of Physiology and Pharmacology*, 61:1089–1092.

Olson et al. (1983b), "Estradiol-17β and 2-hydroxyestradiol-17β-induced differential production of prostaglandins by cells dispersed from human intrauterine tissues at parturition," *Prostaglandins*, 25:639–651.

Olson et al. (1983c), "Prostaglandin output in relation to parturition by cells dispersed from human intrauterine tissues," *Journal of Clinical Endocrinology and Metabolism*, 57:694–699.

Robinson et al. (1979), "The concentrations of the prostaglandins E and F, 13,14-dihydro-15-oxo prostaglandin F and Thromboxane $B_2$ in tissues obtained from women with and without preeclampsia," *Prostaglandins and Medicine*, 3:223–234.

Siler-Khodr and Forman, "Effect of IGF-1 on placental prostanoid production," *Prostaglandins*, 46:361–369, 1993.

Siler-Khodr et al. (1986a), "Differential inhibition of human placental prostaglandin release in vitro by a GnRH antagonist," *Prostaglandins*, 31:1003–1010.

Siler-Khodr et al. (1986b), "GnRH effects on placental hormones during gestation. III. Prostaglandin E, prostaglandin F, and 13,14-dihydro-15-keto- prostaglandin F," *Biology of Reproduction*, 35:312–319.

Siler-Khodr et al. (1986), "Gonadotropin-releasing hormone effects on placental hormones during gestation. I. Alpha-human chorionic gonadotropin, human chorionic gonadotropin and human chorionic somatomammotropin, " *Biol. Reprod.*, 34:245–54.

Straus et al., "Expression of the genes for insulin-like growth factor-1 (IGF-1), IGF-2, and IGF-binding proteins-1 and -2 in fetal rats under conditions of intrauterine growth retardation caused by maternal fasting," *Endocrinology*, 128:518–525, 1991.

Valenzuela G. & Bodhke R. R. (1980), "Effect of pregnancy-induced hypertension upon placental prostaglandin metabolism: decreased prostaglandin $F_{2\alpha}$ catabolism with normal prostaglandin $E_2$ catabolism," *American Journal of Obstetrics and Gynecology*, 136:255–256.

Verhaeghe et al., "C-peptide, insulin-like growth factors I and II and insulin-like growth factor binding protein-1 in umbilical cord serum: correlations with birth weight," *Am. J. Obstet. Gynecol.*, 169:89–97, 1991.

Walsh S. W. (1985), "Preeclampsi: an imbalance in placental prostacyclin and thromboxane production," *American Journal of Obstetrics and Gynecology*, 152:335–340.

Walsh et al. (1985), "Placental prostacyclin production in normal and toxemic pregnancies," *American Journal of Obstetrics and Gynecology*, 151:110–115.

Wang et al., "The concentration of insulin-like growth factor-1 (IGF-1) and insulin-like growth factor binding protein-1 (IGFBP-1) in human umbilical cord serum at delivery: relation to fetal weight," *J. Endocrinol.*, 129:459–464, 1991.

Walsh S. W. & Coulter S. (1989), "Increased placental progesterone may cause decreased placental prostacyclin production in preeclampsia," *Am J. Obstet. Gynecol.*, 161:1586–92.

What is claimed is:

1. A method for treating hypertension in a pregnant animal comprising administering to the animal a pharmacologically effective concentration of insulin-like growth factor to inhibit thromboxane and prostaglandin $F_{2\alpha}$ production without inhibiting prostaglandin E or prostacyclin production.

2. The method of claim 1 wherein the insulin-like growth factor is IGF-I, IGF-II, or an analog thereof.

3. The method of claim 1 wherein the insulin-like growth factor is IGF-I.

4. The method of claim 1 wherein the animal is a human.

5. The method of claim 1 wherein the production of human chorionic gonadotropin and PGFM is unaffected.

6. The method of claim 1 wherein the pharmacologically effective concentration of insulin-like growth factor is between about $10^{-7}$ to about $10^{-10}$ M.

7. The method of claim 1 wherein the insulin-like growth factor is administered subcutaneously, intramuscularly, intravenously or intra-amniotically.

8. The method of claim 1 wherein the insulin-like growth factor is administered in a pharmacologically acceptable carrier solution.

* * * * *